United States Patent
Wei et al.

(10) Patent No.: US 6,756,213 B1
(45) Date of Patent: Jun. 29, 2004

(54) NUCLEIC ACID ENCODING RETINOIC ACID RECEPTOR

(75) Inventors: Ming-Hui Wei, Germantown, MD (US); Jane Ye, Boyds, MD (US); Chunhua Yan, Boyds, MD (US); Karen A. Ketchum, Germantown, MD (US); Valentina Di Francesco, Rockville, MD (US); Ellen M. Beasley, Damestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/691,220

(22) Filed: Oct. 19, 2000

Related U.S. Application Data

(60) Provisional application No. 60/239,117, filed on Oct. 11, 2000.

(51) Int. Cl.[7] .............................. C12N 5/10; C12N 15/12
(52) U.S. Cl. ................... 435/69.1; 435/320.1; 435/325; 536/23.5
(58) Field of Search ...................... 536/23.5; 435/320.1, 435/69.1, 325

(56) References Cited

FOREIGN PATENT DOCUMENTS

WO    WO 02 57454 A    7/2002

OTHER PUBLICATIONS

Database EMBL Online! "Human PML/alpha–RAR Fusion Gene, SEQ ID No. 13." DNA, 3511bp. Sep. 11, 2000. Database accession No. AAA38656. XP002233349.
Database EMBL Online! "Human mRNA for Receptor of Retinoid Acid." RNA, 2907 bp. Oct. 25, 1998. Database accession No. X06614. XP00223350.
Giguere et al. "Identification of a Receptor for the Morphogen Retinoid Acid." Nature, vol. 330, 1987, pp. 624–629. XP001146255.
Database EMBL Online! "Human PML–RAR Protein mRNA, Complete CDs." RNA, 3036 bp, Sep. 14, 1991. Database accession No. M73779. XP002233351.
Kakizuka A. et al. "Chromosomal Translocation t (15;17) in Human Acute Promyelocytic Leukemia Fuses RAR Alpha with a Novel Putative Transcription Factor, PML." Cell, vol. 66, No. 4, 1991, pp. 663–674. XP001146256.
Database EMBL Online! "Rattus Norvegicus Retinoic Acid Receptor Alpha 2 Isoform (RAR) mRNA." DNA, 2130 bp, Jun. 15, 1998. Database accession No. U15211. XP002233352.
Akmal K.M. et al. "Region–Specific Localization of Retinoid Acid Receptor–Alpha Expression in the Rat Epididymis." Biol. Reprod., vol. 54, No. 5, 1996, pp. 1111–1119. XP000901245.
Database EMBL Online! "Homo Sapiens Chromosome 17 Clone RP5–1112G21 Map 17, Working Draft." DNA, 158766, Nov. 18, 1999. Database accession No. AC015851. XP002233353.
Database EMBL Online! "Human REMAP–1 Gene (Incyte ID No.: 71924779CB1)." DNA, 2192 bp, Oct. 21, 2002. Database accession No. ABS51288. XP002233354.
Chambon P. "A Decade of Molecular Biology of Retinoid Acid." FASEB Journal, Vol. 10, No. 9, 1996, pp. 940–954. XP009007018.

*Primary Examiner*—Michael Pak
(74) *Attorney, Agent, or Firm*—Celera Genomics; Justin D. Karjala

(57) ABSTRACT

The present invention provides amino acid sequences of peptides that are encoded by genes within the human genome, the nuclear hormone receptor peptides of the present invention. The present invention specifically provides isolated peptide and nucleic acid molecules, methods of identifying orthologs and paralogs of the nuclear hormone receptor peptides, and methods of identifying modulators of the nuclear hormone receptor peptides.

9 Claims, 13 Drawing Sheets

```
   1 AACAGCACGA GGGCGAGGGG ACGTCTCCTC TCCCCCAGCT GCTCTGCTCG
  51 GATGGCGCCG CCGGCTGAGT GACGGGGGCG GCGCGCAGGA CTTCCCAGCT
 101 CGGACCTCTT GCCTTCGAGG GGAAAGATGT ACGAGAGTGT AGAAGTGGGG
 151 GGTCCCACCC CTAATCCCTT CCTAGTGGTG GATTTTTATA ACCAGAACCG
 201 GGCCTGTTTG CTCCCAGAGA AGGGGCTCCC CGCCCCGGGT CCGTACTCCA
 251 CCCCGCTCCG GACTCCGCTT TGGAATGGCT CAAACCACTC CATTGAGACC
 301 CAGAGCAGCA GTTCTGAAGA GATAGTGCCC AGCCCTCCCT CGCCACCCCC
 351 TCTACCCCGC ATCTACAAGC CTTGCTTTGT CTGTCAGGAC AAGTCCTCAG
 401 GCTACCACTA TGGGGTCAGC GCCTGTGAGG GCTGCAAGGG CTTCTTCCGC
 451 CGCAGCATCC AGAAGAACAT GGTGTACACG TGTCACCGGG ACAAGAACTG
 501 CATCATCAAC AAGGTGACCC GGAACCCCTG CCAGTACTGC CGACTGCAGA
 551 AGTGCTTTGA AGTGGGCATG TCCAAGGAGT CTGTGAGAAA CGACCGAAAC
 601 AAGAAGAAGA AGGAGGTGCC CAAGCCCGAG TGCTCTGAGA GCTACACGCT
 651 GACGCCGGAG GTGGGGGAGC TCATTGAGAA GGTGCGCAAA GCGCACCAGG
 701 AAACCTTCCC TGCCCTCTGC CAGCTGGGCA AATACACTAC GAACAACAGC
 751 TCAGAACAAC GTGTCTCTCT GGACATTGAC CTCTGGGACA AGTTCAGTGA
 801 ACTCTCCACC AAGTGCATCA TTAAGACTGT GGAGTTCGCC AAGCAGCTGC
 851 CCGGCTTCAC CACCCTCACC ATCGCCGACC AGATCACCCT CCTCAAGGCT
 901 GCCTGCCTGG ACATCCTGAT CCTGCGGATC TGCACGCGGT ACACGCCCGA
 951 GCAGGACACC ATGACCTTCT CGGACGGGCT GACCCTGAAC CGGACCCAGA
1001 TGCACAACGC TGGCTTCGGC CCCCTCACCG ACCTGGTCTT TGCCTTCGCC
1051 AACCAGCTGC TGCCCCTGGA GATGGATGAT GCGGAGACGG GGCTGCTCAG
1101 CGCCATCTGC CTCATCTGCG GAGACCGCCA GGACCTGGAG CAGCCGGACC
1151 GGGTGGACAT GCTGCAGGAG CCGCTGCTGG AGGCGCTAAA GGTCTACGTG
1201 CGGAAGCGGA GGCCCAGCCG CCCCCACATG TTCCCCAAGA TGCTAATGAA
1251 GATTACTGAC CTGCGAAGCA TCAGCGCCAA GGGGGCTGAG CGGGTGATCA
1301 CGCTGAAGAT GGAGATCCCG GGCTCCATGC CGCCTCTCAT CCAGGAAATG
1351 TTGGAGAACT CAGAGGGCCT GGACACTCTG AGCGGACAGC CGGGGGGTGG
1401 GGGGCGGGAC GGGGGTGGCC TGCCCCCCCC GCCAGGCAGC TGTAGCCCCA
1451 GCCTCAGCCC CAGCTCCAAC AGAAGCAGCC CGGCCACCCA CTCCCCGTGA
1501 CCGCCCACGC CACATGGACA CAGCCCTCGC CCTCCGCCCC GGCTTTTCTC
1551 TGCCTTTCTA CCGACCATGT GACCCCGCAC CAGCCCTGCC CCCACCTGCC
1601 CTCCCGGGCA GTACTGGGGA CCTTCCCTGG GGGACGGGGA GGGAGGAGGC
1651 AGCGACTCCT TGGACAGAGG CCTGGGCCCT CAGTGGACTG CCTGCTCCCA
1701 CAGCCTGGGC TGACGTCAGA GGCCGAGGCC AGGAACTGAG TGAGGCCCCT
1751 GGTCCTGGGT CTCAGGATGG GTCCTGGGGG CCTCGTGTTC ATCAAGACAC
1801 CCCTCTGCCC AGCTCACCAC ATCTTCATCA CCAGCAAACG CCAGGACTTG
1851 GCTCCCCCAT CCTCAGAACT CACAAGCCAT TGCTCCCCAG CTGGGGAACC
1901 TCAACCTCCC CCCTGCCTCG GTTGGTGACA GAGGGGGTGG GACAGGGGCG
1951 GGGGGTTCCC CCTGTACATA CCCTGCCATA CCAACCCCAG GTATTAATTC
2001 TCGCTGGTTT TGTTTTTATT TTAATTTTTT TGTTTTGATT TTTTTAATAA
2051 GAATTTTCAT TTTAAGCACA AAAAAAAAAA AAAAAA
```

FEATURES:
Start codon: 127
Stop codon: 1498

FIGURE 1, page 1 of 2

Homologous proteins:
Top 10 BLAST Hits

```
                                                                    Score    E
gi|3213188|gb|AAC23439.1|  (U15211) retinoic acid receptor alpha...  918   0.0
gi|4506419|ref|NP_000955.1| retinoic acid receptor, alpha >gi|1...   830   0.0
gi|35874|emb|CAA29787.1|   (X06538) retinoic acid receptor (AA 1 ... 830   0.0
gi|7638251|gb|AAF65452.1|  (AF242867) ECFP-retinoic acid recepto...  830   0.0
gi|7441783|pir||S78481 retinoic acid receptor alpha-2 - eastern...   829   0.0
gi|4160009|gb|AAD05222.1|  (AF088895) retinoic acid receptor alp...  829   0.0
gi|1314308|gb|AAB00112.1|  (U41742) nucleophosmin-retinoic acid ...  827   0.0
gi|8815561|gb|AAB19602.2|  (S50916) retinoic acid receptor alpha...  827   0.0
gi|1314310|gb|AAB00113.1|  (U41743) nucleophosmin-retinoic acid ...  827   0.0
gi|190125|gb|AAA60126.1|   (M73779) PML-RAR protein [Homo sapiens]   827   0.0
gi|545176|gb|AAB29813.1| retinoic acid receptor alpha, RAR alph...   824   0.0
gi|2119682|pir||I50674 retinoic acid receptor alpha isoform 2-1...   819   0.0
gi|1743345|emb|CAA71177.1| (Y10094) retinoic acid receptor-alph...   816   0.0
gi|133484|sp|P11416|RRA_MOUSE RETINOIC ACID RECEPTOR ALPHA (RAR...   815   0.0
```

EST:
```
gi|847367|gb|R73335.1|R73335 y110b08.r1 Soares breast 2NbHBst H...    708   0.0
gi|2714987|gb|AA705069.1|AA705069 zj83e11.s1 Soares_fetal_liver...    517   e-144
gi|8636851|gb|BE174125.1|BE174125 QV1-HT0572-200300-117-c12 HTO...    466   e-128
gi|2841314|gb|AA781983.1|AA781983 ai78g12.s1 Soares_testis_NHT ...    297   5e-78
gi|611497|gb|T29399.1|T29399 EST79267 Human Placenta Homo sapie...    123   2e-25
gi|1969924|gb|AA317545.1|AA317545 EST19547 Retina II Homo sapie...     80   2e-12
```

EXPRESSION INFORMATION FOR MODULATORY USE:
library source:

| | |
|---|---|
| gi|847367|gb|R73335.1 | Human Breast |
| gi|2714987|gb|AA705069.1 | Human fetal liver-spleen |
| gi|8636851|gb|BE174125.1 | Human head-neck |
| gi|2841314|gb|AA781983.1 | Human testis |
| gi|611497|gb|T29399.1 | Human placenta |
| gi|1969924|gb|AA317545.1 | Human retina |

Expression information from PCR-based tissue screening panels
Human Brain
Human Placenta
Human Liver
Human Hela cells
Human Kidney FIGURE 1, page 2 of 2

```
  1 MYESVEVGGP TPNPFLVVDF YNQNRACLLP EKGLPAPGPY STPLRTPLWN
 51 GSNHSIETQS SSSEEIVPSP PSPPPLPRIY KPCFVCQDKS SGYHYGVSAC
101 EGCKGFFRRS IQKNMVYTCH RDKNCIINKV TRNPCQYCRL QKCFEVGMSK
151 ESVRNDRNKK KKEVPKPECS ESYTLTPEVG ELIEKVRKAH QETFPALCQL
201 GKYTTNNSSE QRVSLDIDLW DKFSELSTKC IIKTVEFAKQ LPGFTTLTIA
251 DQITLLKAAC LDILILRICT RYTPEQDTMT FSDGLTLNRT QMHNAGFGPL
301 TDLVFAFANQ LLPLEMDDAE TGLLSAICLI CGDRQDLEQP DRVDMLQEPL
351 LEALKVYVRK RRPSRPHMFP KMLMKITDLR SISAKGAERV ITLKMEIPGS
401 MPPLIQEMLE NSEGLDTLSG QPGGGGRDGG GLPPPPGSCS PSLSPSSNRS
451 SPATHSP
```

FEATURES:
Functional domains and key regions:

| InterPro | Results of FPrintScan against PRINTS | Results of HMMPfam against PFAM-A | Results of PPsearch against PROSITE | Results of ProfileScan against PROSITE profiles |
|---|---|---|---|---|
| IPR000003 Retinoic acid receptor | PR00545 [149-163] [340-357] [361-380] | | | |
| IPR000324 Vitamin D receptor | PR00350 [83-99] [100-119] | | | |
| IPR000536 Ligand-binding domain of nuclear hormone receptor | | PF00104 [225-383] | | |
| IPR001628 C4-type steroid receptor zinc finger | PR00047 [83-99] [99-114] [132-140] [140-148] | PF00105 [81-156] | PS00031 [83-109] | |
| IPR001723 Steroid hormone receptor | PR00398 [144-154] [226-247] [247-263] [314-329] [371-388] | | | |

Membrane spanning structure and domains:
```
Helix Begin   End   Score Certainty
   1    292   312   0.641 Putative
```

FIGURE 2, page 1 of 3

BLAST Alignment to Top Hit:
>gi|3213188|gb|AAC23439.1| (U15211) retinoic acid receptor alpha 2
            isoform [Rattus norvegicus]
            Length = 459

Score =  918 bits (2347), Expect = 0.0
 Identities = 445/457 (97%), Positives = 449/457 (97%), Gaps = 2/457 (0%)
 Frame = +1

```
Query: 1     MYESVEVGG--PTPNPFLVVDFYNQNRACLLPEKGLPAPGPYSTPLRTPLWNGSNHSIET 174
             MYESVEVGG  P PNPFLVVDFYNQNRACLL EKGLPAPGPYSTPLRTPLWNGSNHSIET
Sbjct: 1     MYESVEVGGLTPAPNPFLVVDFYNQNRACLLQEKGLPAPGPYSTPLRTPLWNGSNHSIET 60

Query: 175   QSSSSEEIVPSPPSPPPLPRIYKPCFVCQDKSSGYHYGVSACEGCKGFFRRSIQKNMVYT 354
             QSSSSEEIVPSPPSPPPLPRIYKPCFVCQDKSSGYHYGVSACEGCKGFFRRSIQKNMVYT
Sbjct: 61    QSSSSEEIVPSPPSPPPLPRIYKPCFVCQDKSSGYHYGVSACEGCKGFFRRSIQKNMVYT 120

Query: 355   CHRDKNCIINKVTRNPCQYCRLQKCFEVGMSKESVRNDRNKKKKEVPKPECSESYTLTPE 534
             CHRDKNCIINKVTRN CQYCRLQKCFEVGMSKESVRNDRNKKKKE PKPECSESYTLTPE
Sbjct: 121   CHRDKNCIINKVTRNRCQYCRLQKCFEVGMSKESVRNDRNKKKKETPKPECSESYTLTPE 180

Query: 535   VGELIEKVRKAHQETFPALCQLGKYTTNNSSEQRVSLDIDLWDKFSELSTKCIIKTVEFA 714
             VGELIEKVRKA+QETFPALCQLGKYTTNNSSEQRVSLDIDLWDKFSELSTKCIIKTVEFA
Sbjct: 181   VGELIEKVRKANQETFPALCQLGKYTTNNSSEQRVSLDIDLWDKFSELSTKCIIKTVEFA 240

Query: 715   KQLPGFTTLTIADQITLLKAACLDILILRICTRYTPEQDTMTFSDGLTLNRTQMHNAGFG 894
             KQLPGFTTLTIADQITLLKAACLDILILRICTRYTPEQDTMTFSDGLTLNRTQMHNAGFG
Sbjct: 241   KQLPGFTTLTIADQITLLKAACLDILILRICTRYTPEQDTMTFSDGLTLNRTQMHNAGFG 300

Query: 895   PLTDLVFAFANQLLPLEMDDAETGLLSAICLICGDRQDLEQPDRVDMLQEPLLEALKVYV 1074
             PLTDLVFAFANQLLPLEMDDAETGLLSAICLICGDRQDLEQPD+VDMLQEPLLEALKVYV
Sbjct: 301   PLTDLVFAFANQLLPLEMDDAETGLLSAICLICGDRQDLEQPDKVDMLQEPLLEALKVYV 360

Query: 1075  RKRRPSRPHMFPKMLMKITDLRSISAKGAERVITLKMEIPGSMPPLIQEMLENSEGLDTL 1254
             RKRRPS+PHMFPKMLMKITDLRSISAKGAERVITLKMEIPGSMPPLIQEMLENSEGLDTL
Sbjct: 361   RKRRPSQPHMFPKMLMKITDLRSISAKGAERVITLKMEIPGSMPPLIQEMLENSEGLDTL 420

Query: 1255  SGQPGGGGRDGGGLPPPPGSCSPSLSPSSNRSSPATHSP 1371
             SGQ GGG RDGGGL PPPGSCSPSLSPSS+RSSPAT SP
Sbjct: 421   SGQSGGGTRDGGGLAPPPGSCSPSLSPSSHRSSPATQSP 459
```

FIGURE 2, page 2 of 3

Hmmer results:

| Model | Description | Score | E-value | N |
|---|---|---|---|---|
| CE00550 | CE00550 retinoic_acid_receptor | 1204.3 | 0 | 1 |
| CE00342 | E00342 retinoid_X_receptor | 341.6 | 6.8e-99 | 2 |
| PF00104 | Ligand-binding domain of nuclear hormone rec | 241.4 | 1.3e-68 | 1 |
| PF00105 | Zinc finger, C4 type (two domains) | 192.6 | 1.2e-56 | 2 |
| CE00055 | CE00055 peroxisome_proliferator_activated_re | 132.1 | 4.9e-45 | 3 |
| CE00059 | CE00059 pregnane_steroid_receptor | 126.1 | 4.3e-37 | 2 |
| CE00544 | CE00544 estrogen_receptor | 94.9 | 1.9e-27 | 2 |
| CE00547 | CE00547 steroid_receptor_Ad4BP | 89.7 | 1.2e-26 | 1 |
| CE00543 | CE00543 steroid_receptor_N10 | 85.2 | 2.3e-36 | 2 |
| CE00036 | CE00036 androstane_receptor | 69.3 | 5e-25 | 2 |
| CE00208 | CE00208 Progesterone_receptors | 54.8 | 3.8e-15 | 2 |
| CE00339 | E00339 vitamin_D_receptor | 43.7 | 3.4e-12 | 2 |
| CE00546 | CE00546 glucocorticoid_receptor | 40.1 | 1.3e-10 | 2 |
| CE00545 | CE00545 progesteron_receptor | 36.9 | 3.4e-11 | 2 |
| CE00386 | E00386 mineralocorticoid_receptor | 10.2 | 0.31 | 1 |
| PF00907 | T-box | 3.8 | 4 | 1 |
| CE00341 | E00341 seven-up_receptor | 3.4 | 3 | 1 |

Parsed for domains:

| Model | Domain | seq-f | seq-t | hmm-f | hmm-t | score | E-value |
|---|---|---|---|---|---|---|---|
| CE00341 | 1/1 | 82 | 97 .. | 175 | 190 .. | 3.4 | 3 |
| CE00545 | 1/2 | 81 | 148 .. | 580 | 647 .. | 25.6 | 8.9e-08 |
| CE00546 | 1/2 | 81 | 148 .. | 438 | 514 .. | 26.8 | 5.9e-07 |
| CE00208 | 1/2 | 81 | 148 .. | 568 | 635 .. | 47.1 | 5.6e-13 |
| CE00386 | 1/1 | 88 | 149 .. | 1 | 66 [. | 10.2 | 0.31 |
| CE00055 | 1/3 | 83 | 149 .. | 109 | 174 .. | 91.7 | 3.4e-31 |
| CE00036 | 1/2 | 83 | 150 .. | 21 | 88 .. | 53.5 | 2.7e-19 |
| CE00339 | 1/2 | 83 | 151 .. | 32 | 100 .. | 43.2 | 4.8e-12 |
| CE00543 | 1/2 | 83 | 156 .. | 327 | 400 .. | 75.4 | 2.7e-32 |
| CE00059 | 1/2 | 83 | 156 .. | 39 | 113 .. | 73.5 | 2e-21 |
| PF00105 | 1/2 | 81 | 156 .. | 1 | 77 [] | 190.7 | 4.3e-56 |
| CE00544 | 1/2 | 83 | 157 .. | 189 | 263 .. | 75.4 | 9.8e-22 |
| CE00547 | 1/1 | 83 | 157 .. | 13 | 87 .. | 89.7 | 1.2e-26 |
| CE00342 | 1/2 | 83 | 200 .. | 1 | 122 [. | 158.3 | 2e-45 |
| PF00907 | 1/1 | 212 | 228 .. | 1 | 18 [. | 3.8 | 4 |
| CE00545 | 2/2 | 235 | 255 .. | 745 | 765 .. | 3.3 | 0.6 |
| CE00546 | 2/2 | 231 | 256 .. | 599 | 624 .. | 2.6 | 3.1 |
| CE00055 | 2/3 | 236 | 257 .. | 297 | 318 .. | 14.7 | 9e-05 |
| CE00544 | 2/2 | 238 | 264 .. | 372 | 398 .. | 9.5 | 0.027 |
| CE00036 | 2/2 | 237 | 264 .. | 185 | 212 .. | 12.5 | 0.00017 |
| CE00208 | 2/2 | 226 | 266 .. | 724 | 764 .. | 3.8 | 1 |
| CE00543 | 2/2 | 242 | 291 .. | 494 | 543 .. | 0.5 | 0.43 |
| PF00105 | 2/2 | 326 | 334 .. | 1 | 9 [. | 5.4 | 2.7 |
| CE00055 | 3/3 | 314 | 380 .. | 376 | 442 .. | 15.4 | 5.3e-05 |
| PF00104 | 1/1 | 225 | 383 .. | 1 | 167 [] | 241.4 | 1.3e-68 |
| CE00059 | 2/2 | 235 | 414 .. | 253 | 432 .] | 47.4 | 1.2e-13 |
| CE00342 | 2/2 | 223 | 416 .. | 119 | 313 .] | 176.7 | 8.7e-51 |
| CE00339 | 2/2 | 323 | 417 .. | 348 | 443 .] | -0.7 | 31 |
| CE00550 | 1/1 | 55 | 457 .] | 97 | 509 .] | 1204.3 | 0 |

FIGURE 2, page 3 of 3

```
   1  GTCCTTGGGT AGCATGTACA TTTCCATCCC TTCCTTTTAT ATATGGGGGT
  51  AATAGGATAC CCCCTCCTCC AGGGGTATCC CCTCTTTCTA GGGACCTACC
 101  CAAGCTAGGC CTTTCTTCCA GTGAAACGTG CATCCCGAGG GCTTCTAGGA
 151  TGAAGTAGTC CACTGGAAGG CACCAGCTCT TCCTTTTATC TCTCCAGAGC
 201  TGGACAGTGC ACCAGGGGCC GGTACTGGTT CCCCAGCTAG GAGACACCTT
 251  GGGCGGGGCT TTGCTCGCCG GAAGCACGCA GAGCGTGGGG AGGAGGGCCC
 301  CCTCTGCCTG TGTTTGTGCC AACAGCACCC GCGCTGCCGC GTCGGGTTCC
 351  GGCGGCCGGA GTCACACATG ATGTCACAGA CAATGACACA AGCCGGTGTC
 401  TCATTCCGAC ACAGCGTCCG AGCTGCACAA TGTCACACCC GGGTGCCAAA
 451  CACTTGGCCC CGCGCGACCC GGCCCTACGC CTCCTGCCGC CGCTCTCCGC
 501  GTCTCCGGGG GAGGTGGCCC GGTTCGGCCG GGCAGGGGGC TGGCGGGCGA
 551  GCCCCGCGGG CGGGCTGGCG AGCGGGTGAT GTCACGGGCA GCGGTGGGTG
 601  GGTCACTCGG AGGTGAGGCG CCGCCAGGCG AGTTCAGCGA GAGTTCAGCC
 651  GCATTGCATT AGGCAAATGA GGCCCGGCCT GGGTGGGGGT GTGTGTTAAG
 701  GGGAGGACAC CGGGACCACC CCCCTCTTCC CCGCCCCACC ACCTCCTCCA
 751  CCACGGCTTC GCTCGGCCAG GGACTGACCA AACCTTGGGG GAGCCTGGGA
 801  GCCGGAACTG GTACAAGGGG AGGACGCCCG CCCTCTTCC GTCCTTGTCC
 851  CCTCGCAGCC CCCTCCTCTC CCTGTACTCG GCGTCCCTCT GTACTCTGTG
 901  TACTCCTCAT CTGGAGCCTT TCCCCCTTCC TGCTTCTCTC CTCTCCTCCC
 951  CCTTCCCAGG CTGCCCCCAC TTGCCTGTCC ACATGCCGCC TCTCCCTCTC
1001  GGTTCCCTGC GTTTCTCCCG CTGCAGCCGG ACGCGCCGGG AATGGGTTAA
1051  GCCAGGGGCG GTGCCTGGAC GGGGCGGGGC GGTGGAAAGG GGGTGGTGCC
1101  CGGAGGGGAG GGGGCGCGCA GAGCTGGGGT GGGGGGGCCG TGGCGCGTAC
1151  CACCAGAGAC CGAGCGAGTC GCCAGCTGCC CCTGGCCTGG CGGGGGCGGA
1201  ACCGCGCGGG ATCCCCACCC CCACCCGGAA TCCTCGCCAC GGAGAATCCC
1251  TGGAGAAGCC CCGGATCCCC GGCTGGGAGG AGGAAGTGCT CGTTGACCCC
1301  CAGCCCCGCG CTGATCCCGC CCCCGGCCTG CGGACTTGGG GAGCCGCTGT
1351  ACTCTGCCTC GGACGCCACG AGACTCTAGA CGGGAGTCCC CTCGAGGTGA
1401  AGCCGCTGAG TTCCCGGGCC CCGCCAGGCT TCCCTGGGAG AGCCGACGGA
1451  CCCCCCCTCC CAGCACACAC AACTTCCCTG CTTTTCACCG GGACTGGCGG
1501  AGCGGCCGGC GGACTTAGAC GCGGGGACTT CAGGGCAGGG GGCGCCCCT
1551  GCCCGGGTCA CCAGTCGGGG CGAGGGGACG TCTCCTCTCC CCCAGCTGCT
1601  CTGCTCGGAT GGCGCCGCCG GCTGAGTGAC GGGGGCGGCG CGCAGGACTT
1651  CCCAGCTCGG ACCTCTTGCC TTCGAGGGGA AAGATGTACG AGAGTGTAGA
1701  AGTGGGGGGT CCCACCCCTA ATCCCTTCCT AGTGGTGGAT TTTTATAACC
1751  AGAACCGGGC CTGTTTGCTC CCAGAGAAGG GGCTCCCCGC CCCGGGTCCG
1801  TACTCCACCC CGCTCCGGAC TCCGCTTTGG AATGGCTCAA ACCACTGTAC
1851  GTACCGGCCT CTCAGTCTGC TGTTGTAGGG GGTGGGAGTG GGCGGTAGGG
1901  CTTCCACTAC TACTCGGGGG TGAGAGTCCC GGGGTGTAGT GGAGGTCCTG
1951  TCTCTACCTT TCACTTAACC CGTGTTGCCC TTGCTGGACA ATTGAACCCT
2001  CCCGCCGCA CCCTCCCCCC AGTAACCCTA AGTGCAATTT GTGTTAGATT
2051  AGGGCTGAGG AACTTTGAGA GTTCCTTCTT TTCAAGCAAC ATTCCTTTCA
2101  TCTCTTTGTT TCACTTCTTC CCAGGAGAAA TGAAGCCCAA GCCCCCTTTG
2151  GCCCCCAGTT TGTATATTCT TTCTTGGCCT TGGGAAATCC CAAAAAGGTT
2201  TCACCAGCAA GGCTTGGGAA GGGGTGGGGG GGTAAAAGGG TTCCCTGGTC
2251  TTGTGGTGGG TTTTTGGTCT TGCTTACCCG GGGGGNNNN NNNNNNNNN
2301  NNNNNNNNNN NNNNNNNNNN NNNNNNNNNN NNNNNNGAAG GGCTCTGTGC
2351  ACACTCAGGA GCTCGGAGCA CCAGGGTGTA CACCTGGGCA TTTTCCTGCG
2401  CAGCTGTGAG GCAGTGTACA CTGGGTGGGC GGGAGCAGGC GCAAGGGGGT
2451  TATTGTTAGA TGGCTCAGGT TTCTTCCCCT CCTGGGCTTT GGGCTCTTTG
2501  CTGGAGGGGA AGCTCTTCCG TGGAGGATCT CCCACCTTCC TGGACCTGCT
2551  GCCTCCCTCC TGCCTGCCAG GGAGGAGGGG TGGAGTGGGT CTCGGGGGGG
2601  CCCTGGCAGA TTGGAAAAGG TTGAAGGGCA AAGGACTTAC CCCACCCCTC
2651  TTGCTGGGAG AAGAGAGACC TGAGATGGAC AGACAGCCCA CCTCTGCCCT
2701  CCCAGAGCCA CTTCTATCCC AGCTTTTCCT ATTGTCCTGC CCCCGACCAT
2751  TTCCTCTAGG GCCGAATCTG CTGTGTGGCT GTAGACACAA GAGGGAAGGT
2801  ATCACCCTTG ACTTTGGAAG AAGAGAGAGT GAGAGGATGA CTCTAGGACC
2851  CTTTTTCTCA TTCTCCCAGT GCTGGAGCAA GACCCCCCTC CCCTAGGGGG
2901  ATAGTTGGAG CAGGGCTGCC CAGAGTCACC CCTTCCACTG CCTTGGCCAC
2951  CTTCTCCAGA GGGCTGGAGA GAAGCTGGGA TCTGAGACCT TGGTCTCCAG
3001  CCCCTGTCTC TTCTTAGCCC ATGGGACAG CTCAGCTCTT CCTGGCCCAG
3051  AACTGGAGAG GGAGGAGGAT CACAGAGAGT AGGACAGGCA GTGTATTGGT
3101  GAGCCCTTCC CCTAAACCAC TGGACATGGG GAAGTGGAGA CCTGTCCCCA
```

FIGURE 3, page 1 of 8

```
3151  CATCCATTCT GGGGTGGGGT AGTAGACCTA GAGGCCTGGG TTTCCAGTTC
3201  CCGTAGTCTG AGCGTGGGTG TGCATATATA AGTGAGTGAG GTGTCAGTGG
3251  ACTCGGGTCC TGAGGCTGTG AGGTTGGGAG TGATGGGGGT CTGGGGGCTT
3301  GCCTTGAGGC ACAGGAAGGA CCCGGAGTCT GAGGGTGGCA ACTAGACTCA
3351  GTCTAGAATA TGTGGGGCCA ATGCCACCAC CTTGGAAGGG TCCCCTTGGG
3401  TGTGTTGGAA GTCCGCTGGT GACTGGAGCT GCCTCCAGCC CCCTCTTGGG
3451  GAATTCTCCA CTCTCCCCTT TACTGCCACT GAAGGTGGGA AGAGCAGGTT
3501  GGCTCTGGGA GGAGGTGGCC TGGGTTCTGC AGGGCCCTAG GGACATTGCC
3551  TCCCTCCCCA GAGCCCTCAT TTCGGTGCAT TAGAGGACAA GGGGGGGTGC
3601  ACAGGATGTG GCTCCCCATC TGTCTCCCAC CAATCTCCGC CACTCACACC
3651  TCCGCCCGCT CCCAGACGTC AAGAATGTG AAGCACGTGG ATGCCCGTAG
3701  TTGGGGGAGG GGGAGACGCT TATCAGGCGG CCGCTGGGCT AGGGGCCTTC
3751  TTCCGCTGCC GCGGTACACC CAGAGCTACC CCCGCCTCTC CCCGGGAGGA
3801  GGAAGGACGG TACAGAGGGC CCTACGCCCC CTCCCCAACC ATCCCCAGGG
3851  GCTGCGAGGG GAGCTGCGGA GGAGCGGGCG CCAGCTGGAT TGGGAGGGGA
3901  GCCGCTGGCC GGGGGCCCGG CTGATTTCCT GCTGATCTCC TCCAGGAAAC
3951  CGGCCCCTTG TGCGAGCCTG CGAACGGCTC GGGGGCGTGG GGAATCCGGA
4001  GTGGAGCGCT CTGCGCCGCC CGCCCTGCCA GGATGGGGAG CGAGGGAGGG
4051  GCACCCTGGC AGCGTCGGCG GGAGGGGACG CCTGGCTTCC TGGGTCAGTT
4101  CCAGTCCTCT GTTGGGCGCT GGAACTTTGA GCTGAGAAGG TGTGGTCCTT
4151  CTCTAGCCCG AGTCCTTCTG CAGGAAGAGG AGAGATTGGT GGGCTGGGCC
4201  TCTGGGGAGG GAGGTTAGCA GGGATGGGCC AGGCCCGGGC AGTCCCTCCC
4251  CCGTTGGTGT CCCTCCCCAC TCCACCTGTG TGTGCAGGGA GTTATGGCCG
4301  TGTCCTAACT CTTGCAGAGG CTGTGAGGAT TCCGGAGTTC CCCACACCTC
4351  CGGCCTTGGT CCTTGTACCT CACCTCCTTG GACTGCTGGC TGGAGGCCTG
4401  GGGAGGTGGG GCATCGAGCT CTGGGTTCAA AGGGCAGAGC AGGGAAACCT
4451  CAGAGCTGGG TTACCTGGGT GACAGGTGGG GATGTGCTGG AGGTAGGGGG
4501  CAGGCTATGT TACAGCCTCC AAGGCAGTCA AGCTGCCGTT GGGTGGGCTA
4551  AAAGGAGGCC TTGCCCAGCC TAAACTGTAG TCCTTGCCTC TGGTCATCTC
4601  TCCCATTCTG CCAAAAAATA ATTTTAAAAA GCACATTCTC TCAGTTCCGT
4651  AAACACCCTC TGTTGGACTT TGCTTTAGCT CCATGTTTTT ATGGCTTTTT
4701  GCCCTCTAGT CTGTCCCAGG CCTTAGAGCT GTTTACCTCT CATCCTGGTA
4751  TCCCCCATGA CTCCCCATAC CCTAGCTCCC CTCGTGACAT CCCGCTCTGT
4801  ACCCCAAAG CTCCCTCAGT CCTTTCTCCC TCTCCAGTCT GGTTCATTTT
4851  AGAAGTGGGG CCTTGGGAGA GGCGGGGCCC AGGGCAAACG GTGGATTAGG
4901  AGGGGTGGGG AGGTCAGTGC CTTCTTCCTC TGCTTGTCGG AATGCTGACC
4951  AAGATTCTAG GCCATGGTCC CCCCAACCCT CCACATACCC CCTTGCCCTT
5001  GATCTCCCCT CCCCCCACCA GTCTGGATTG TCTATTGTTA CTGCTTTTAC
5051  GTCTTGGAAA AAGTTAGCAC AACAAAGGGC TGCTTTGTGG CTCACCCCCT
5101  CTGCCTCCTG GCCTCACCCA GGCCCCCCAA CCCCGCCCCC CCAGCAGCTG
5151  TTCTCAGGCC TCTCAGCCTG TCTGATTTGC TTGTCTGGCC TGGGGAGAAT
5201  GAGGTGGGAG AAAACCAGGC CAGGGCAGTT GGTGTTGGAG TGAAGAGCAG
5251  ACGGCGGTGG GGAGGTCAGG AGAGAATCTG CTGGGCTGGG GATGGTGTGG
5301  GCATCAACTG TCCCATTGCT GCAGGCTGGT CTTGGGGCAG GGAAGGGGAT
5351  GGGGGGCCAT AGCAGTGCTG GTCAGCCAGG CTGGCCTGGG AAGTGGTGCC
5401  CAGGCACTAC TAAGAGCCAG GAAAGCCCTG CCAAGGTTGT TGGCCTAGTT
5451  CCCTGTCATC AGCCGCCTAG CAGCCCCCAC TGTGTCTGCA GGTAAGGGGG
5501  GAGGGTGGTA GCACATAGTC AGCCCCTGGT GTTCCCATGC TTCCTTCCTC
5551  TGTGCCCCAA TTTTAGGGCC ATGTGATTTG GGCTATGTG ACTCATGTCT
5601  GTAAGGTGCT TGGGCCAGGA GCTGTGGGCA CCTTTAAATG CCAGCCAGTC
5651  TCATGTGCCG GAGTTTGGGG TAGGGCTAGG TAGGATTGTG GAATATGGGA
5701  GGAGGCAGGG ATCTGTCTAC CTAGGGAGGC ATCCTCATCC ATCCTTGGCC
5751  CTGGACAAGA GAACTTGAAC GTTGGTAGGG GCCTCAGGAC GATGCTGCGT
5801  GGCCCCTTGG GAATCTGGGA TTGTCCTGGT CATAGTTCTT ATCTTGCACC
5851  CAACACCCTT AGCTGCCCAG GCTTTGGACA TGGATAGCCC CTACCCAACC
5901  CAGCCCTGTT CTGCCTACAG TGATGGGCAT GGAGCCAGAC ACTGGGGAGG
5951  ATTTGGCCAG TGAGGCTGC CCCTGCTGTC TGGGTCACCC CTCCTGGCTG
6001  CCCTCTTGGA GCTGAATAAC AGAAGGGGAG GGGTTAGTAA CCCGGACATA
6051  GTATTGAGGC CAGACAGACA GAGCATTGAT GGGAACAGAC CCCCTTTGTC
6101  ATGCCATCTC TCCCCAGATG GGGGTACCC AGAATAATGG GCTTTTGGGG
6151  CCCTGGGGAC TCTTCTCCCT GTATTCAGGG TATCTCCCCC TATCTCAGGG
6201  AGACACCTCC TACTGTGCCC AGCATTTGTG ACTCTTCTTT GCACCCCCTG
6251  CCTTGGGTCC CTGCCCTGG GATTGTTTGG GTGGAGGAGG GGCAGTGGCT
```

FIGURE 3, page 2 of 8

```
6301  GCTGGCAGAA TGGGGTGGAG GGGGGAGCGG AAGCAGAGGG GGCGGGGGAG
6351  TGGCCGGCTT TGAATATCCT GTTGACCCCA GTTTCCTCTG CCCCCAGCTT
6401  ATGTCCTCTT CCCTCCCTCC TCTTCAAGCG TTAACTCCTT CCTAACTCGG
6451  GGGGAGAACG GGGCCAGGCC GCCCAGGGGC AGGAGCTTTA GAATCAGGGT
6501  GACCCCCACC CCTACTCCCC AAGCACAGTC ACGGCACACA TACAAATGTG
6551  ATGGTTTATC ATTGTATCTT TGTGGTTTTG AAGGTGGGGG TCCTAGGAGT
6601  CCAGAGGAGT GATGGGGTGC TGGAGGCTTC ATTGGCAGCC TCCTGCCCTG
6651  AGTCTGGCTG GGGAGTCCCA GTTTTCTTAA GACTTGAATC CTGCCAGCAG
6701  TGGTGAGGCT GGGAGAGGCT CTTAGGAGGG ACGGTGAGGC AGGGTGGAGC
6751  TTGGTACTAA GGATGGCGAC CTAGGTCTCT AACTGCCCCT CCCCTCTTCT
6801  CTCTCTAGCC ATTGAGACCC AGAGCAGCAG TTCTGAAGAG ATAGTGCCCA
6851  GCCCTCCCTC GCCACCCCCT CTACCCCGCA TCTACAAGCC TTGCTTTGTC
6901  TGTCAGGACA AGTCCTCAGG CTACCACTAT GGGGTCAGCG CCTGTGAGGG
6951  CTGCAAGGTG AGTTGAAGGG GTCATTGGGA AGGACAGCTT GATGAGGTCA
7001  ATGGGGATGT CCCCACTTCT GTGTCCTGGG AGTGTGCAGT TGGGGGGTGT
7051  CCCTGAATTG CTGCTCTTCT TTCTCTGTGG AAGTTGGCAG CAAGCAGGGG
7101  ACACCTACCA CAGTTTCCCC ACAGGTCCTC CCCCATAAAT GTGCAGGGCT
7151  CCCTCAAACC AGAGGTCCCC TCCTGCCTCA GCTCCTTTCC CTGTCTCTAT
7201  CCTCCAGCTG GCAGGGCGTA CGCCTGCTCT GCCACCGCTG CCCAGGTTGC
7251  CATGGTGAGC TGGCTGCCGA CTGGCTCTTG GCTGGGGACC CAGGAGGCCT
7301  CCCCCGGCGG CCCTGCCTGA ACCTCACCAT GGCAGCCTGG CAGGAGGCAG
7351  TTAGGAGCAG GCACCCTGCC TTAGCTTCCC CTTCAGGTGC CCGGGCTGTG
7401  GGCTCCCCAG TGTCTGGCTG GATTTCCCCA TCCTCACGTT AGGTGCCAGG
7451  GTGCAGGTAT ACCTGGTCCT TAGCAGCCCT GCGCCCGGCT TCTCCTCCTT
7501  TCCCTGGGGC CTGAGCCTCT GTGTGCGTTT CTTCCTCCAG AGATTGGGGC
7551  TCAGAATCTT CACAGCTTTG GGCCTTGCAG CTCTGGGCTG CTCTTCAGCC
7601  TGGAGTAGCT ATCCCCAGAT GTGGGACGGA GGTCAAGGGC AAAGCACAAG
7651  GACTCAGGCT GTGTGTCTGC CTGTCCTGTC TGGTTGTTGT TGGTCTGTTC
7701  TTCCTCTGTC CGCCTGTCCC TCTGGTCAGC CTGTATGTGG AGCCCCTGGC
7751  CAGCCTGGGT CTGTGTCTGT GATGGGTCGG TGCACACCTG TCTTGGTGAA
7801  CTCACATCTT TCTGCCTTGC TCCTGAGTGC ATGTGTGTGT TCGCCTCCAT
7851  TTCTCTGGCC AGCCCGTGTA TCTGCCTCCT GGCCTCTTCG GGCTTGTCTT
7901  CTTTTCCTGT GTTCTGAGTT CAGGGGTGTG GGTTCCAGAT CCCTGGCTGT
7951  TGCCCAGTTA GCCCCATGTC TTCCTATTTC TGACTCACCA GCAGCCCTGA
8001  GGTCTTTTCC CTGGAAGGGA GGAGTCAGGT GTGTGCTGTG GGTTGGGGGA
8051  AGACTCCTGC CCATCCTGCA GTGTTGAGGC AGGTACTGGG ATTCTCCTGA
8101  GGAGGATCCT TTTAGGTGAA TCATTCTCCC CAGCTTTTCT GGCCTGCTCA
8151  GGTAGGCGAT GGGCAAACGC TTGGGGGCAG CAGCTGGCCT GGCCCTCCTC
8201  CCCTAGACTG AGACCGTAGC CAGGCACTGC TCCCACTGTG GGTGTGGACA
8251  ACCTGACTCC CTCCCCTCCA TACCCAGGGC TTCTTCCGCC GCAGCATCCA
8301  GAAGAACATG GTGTACACGT GTCACCGGGA CAAGAACTGC ATCATCAACA
8351  AGGTGACCCG GAACCGCTGC CAGTACTGCC GACTGCAGAA GTGCTTTGAA
8401  GTGGGCATGT CCAAGGAGTG TGAGTGCCAT AGGGCAGGGG CCGAGTCCCG
8451  CCTCAGTTGG GGTCTCAGAT GCTCCTAAAG ACCAAGGGAG CAGGGCTCTG
8501  TGGATGTTTG TGCACATGCA TGAACACGCA TGCCGTGGTG TGCGGGCTCA
8551  CGGTTGAGGA TGGTTTGTGT GTAGCTGCAA GGACCTGTTT GCGAGTCTGG
8601  CTGGCTGTGT GTCCACGGGC AGGTCTGTGC TCCGGGACCG TGTATGTGTA
8651  ACCATTCCTG TTTCTGCACG TCTGGCTGTG TGTGCTTGCG TATGTGTGTG
8701  TGTGTGCATG CTCCAGGATG GCTTTCTTCC AGGCCGTGCT TGGTTTTGGG
8751  GTGGGGCTCA GAGGCATAGG CAGTCCCTTC TGATTGTGAG TCTTAGGGGA
8801  GGGGCTTGAA TTCTGAGGGG TGCTTGGCTG GACTTATGTG TGTATGGGGG
8851  GGTGGAAGGG CTGGCACAAG GATCCAAAAG CCATTGTCTA GTTAAGCCTG
8901  GGATTCAGAG TTGGAAGAAA GAATTGGGAC TTCTCAGATC CCAGAGGAAA
8951  CGGGGTTTCC ACTTTGGGCT CAGCTGAGGC CTGATGGAGG GAGGGAGGGA
9001  AAGGCTGGAC AGGGAGACCC TCTTGTGTTG AATCATGGGT GTTGCCATGG
9051  TGACCGGTGA TTGATGATGT CAGAGATAAA TGACGCTGAC AGACGCCTCC
9101  TTGTCTGCGT GGCCGTTGCC ATGGAGCCTG AGCCTTGGGG GATGGGATGG
9151  GGGAGGGGGC TGCAGGACCC CCTAGCCCTT TGTGGGGAGG GCAGTGGGGA
9201  GGGGGCACGG GTGAGATGGT TCTGACTGTT GCACGAAGAG CCCCAGACAG
9251  GAATGGAGGG GACTGGAGTG TCCTGCCACA GGAGGCTGGG GGTGCCTTGT
9301  CCTGAGCCCA GGAAGTGGTG GCTCCTGCTG CAAGAGTGGG TGACAACTCA
9351  AGACCCACAA GCCTGGAACC CTTCGCTTAA GGGCTGTCAC CTCCTCCTCT
9401  CTGTTTGTGC CACCTTCTGC TCTTTTCATG GCAGAAGGAC CAGGGAGGGG
```

FIGURE 3, page 3 of 8

```
 9451  ACCCCTTCTC CCTCCCACCG CCAACTCCCC TTCTCCCTCC CACCGCCAAC
 9501  TCCCCCTCTC CCGGCTGCTC TGTGCCCCGG AGCTGAGCAG CTGCCATTTC
 9551  AATAGAATTA AAGCTTCCGA ATGATAAACG TCTTGTCACA GCTGCAATTT
 9601  TCTCTTCCCA AATTATCCCC CCACTCTCCC TCTCCCTCTC CCTTCTCTCC
 9651  CCTGCACTTT ATTGAATTTG CAGAATCGAC ATGAGTGATC TCCAAATTAT
 9701  GCCAGCTACC CCCACCTCGC TACCCCCTCC CTGAGCCCCT CCCCCACCCT
 9751  CCCTTCCTCC CGCGTCAGCA GCCACCACCA CCAGCCCTGT GAGTGATTGT
 9801  GTGTCTGGAT AATCGGCTGG TAACGACCCC ATCGCTTCTT TAAAGCCGAG
 9851  TGGTGTGTGC GGCTCAGCGC CCCTGGTGAT TTGTCAGCTC CCCAGCTAAT
 9901  GGGCCAAGAG ATTCTCCCCG CCAGGTCCCC CACTCTCAGG CTGGGGAGCC
 9951  CTACTCCCCA CTTGCCCCAG GAGCTGCTCA GAGCCAGTCC CAAGGGACCC
10001  CCAGGGAGAC TGCAGCTGGG AGGGCTGGGT GAGTGGAGGC GGGAGAAGGA
10051  CCTTCCTGGG GAAAGAGGAG GCAGAGCACC TAGGAGGGCA CCGTCGCCTG
10101  GAGTGTGAGC TGGAGTAGAC GCGTGGGGGA TAGCATGCGG CTGGCTATGG
10151  GGTGGGGTGG GGGGTGTGTG CAGGGCCACA GCTGTGCTCA TGGGGCTTCT
10201  GGGGCAGAAC TTGATGTGTG GGTTGGGTGG GCATGGAGGG CTGGAGTGCG
10251  TGGCAATGCC TTGCCTGCCC GTGAACGCGT GCTGTGTGCG CGTGCTTACA
10301  AGCCTGGGTG ACCTCCTCAG CAGCTGGCAG CTCTCTGTCA GGCTGGGGGT
10351  GGACGAGGCC CTGAGCAGCC TGCAGCTGCC CTCTTAACCC CCTCTGCCCT
10401  CCACAGCTGT GAGAAACGAC CGAAACAAGA AGAAGAAGGA GGTGCCCAAG
10451  CCCGAGTGCT CTGAGAGCTA CACGCTGACG CCGGAGGTGG GGGAGCTCAT
10501  TGAGAAGGTG CGCAAAGCGC ACCAGGAAAC CTTCCCTGCC CTCTGCCAGC
10551  TGGGCAAATA CACTACGGTA TGGCTTTCCC CCGGCCTGCA GGGTGGGATT
10601  TGCCCAGGGC CACAGGGCCA GGATGGGCCC CTCTCAGGCA CCCCTTCTTG
10651  TGCCAGGCAA GATCTCTGCG TCCTTCCCTT CCCCTCTCTT CTCCCTCCTC
10701  CTGCTGCCTC TTCCCAAGGA GCTCCCAGGA AGTGAAGGCT GGGTAGAGGG
10751  CAGGCCTGTG GGGCTGGAG CCAGGCTGAG AAGGGGTGCC ATGGAGAAGA
10801  AGGCCCTCAC TCTCCCTCCT CCCCCAGAAC AACAGCTCAG AACAACGTGT
10851  CTCTCTGGAC ATTGACCTCT GGGACAAGTT CAGTGAACTC TCCACCAAGT
10901  GCATCATTAA GACTGTGGAG TTCGCCAAGC AGCTGCCCGG CTTCACCACC
10951  CTCACCATCG CCGACCAGAT CACCCTCCTC AAGGCTGCCT GCCTGGACAT
11001  CCTGGTGAGG GTCTGCACCC TGGCCCCCAG GCACTGCCCC TGTGTCCTGG
11051  GTAGATGTCC TTCCAGCCAG ACAGCCACCC TCCTAAATGT CTGTCTGCAA
11101  TCAACCTGTC CAAATGCCCA CCGCCCAAAT GTCTGCCCTT CCTCTCCCCA
11151  TATGTCCACC TGTCCACTCG TCTCCCTGTC CACTCAGCCA CCTAGCAGCC
11201  AGATGTGCAG GAGCTCACCT GTTCACCCAT ACACATATCC AGCCACCCAG
11251  CCATCCATCC ATTTAGCCAG TAATAAAGAT TCACGTAGGA GCCAGGTGCA
11301  GTGGCTCATA CCTGTAATCC CAGCACTTTG GGAGGCCGAG CGAGGCAGGA
11351  GGATCACTTG AGGCTGGAAG TTCAAGACCA CCCTGGGCAA CATAGTGAGA
11401  CCTTATTTCT GCAAAAAACT AAAAAGATTC ACCTAGGATC CTCTGGCCAG
11451  TGTTCGAGCT GGGTGTCAGG AACCCAGCGG TGAATGCACC ACCATCCCCT
11501  CTCTTGAAAA CCTTCCATGT GAGGCAAGAG ATAAGTCAAC AGAGGTTGCA
11551  AAACTGTGAT CAATGCTTCC TGGAGATTGG GGGAGGGCTT GTGACTGCTT
11601  GGGCCTGAAG GATGATGTCT CAGAGGAGGT GACATCTAGG GGTTTGTAGA
11651  GGGGGAGGTG AGAGGGTAGC CCTAACTCAG GAGCAGGAAG TGAAAGACTT
11701  GCTGCTGTGA GGCCATGCTG AGCTCAGGGG ACTGCCGGGC ACTCGGTGAG
11751  GTGAGCCCGA GGGTAGACTG GGCTGGAGGC TGGATGCAGG GGGTGGGGGC
11801  AGGAAGAGGT GGTGGGAACT GCCAAAGCCT AGGCTGGAGG GAGCACTCTC
11851  CTTCCTGCTG TCCCTGACAA GGGCTCGGTC CACCTGTTCC CTCTTGGTCA
11901  CCTCCAGGGT GGGGAACCTG GGATTTGACG AGACTGTCAT TTCTTTTTAT
11951  GTTTTTCTTT TTTGAGATGG AGTTTCACTC TTGTCACCCA GGCTGGAGTG
12001  CAGTAGTATG ATCTTGGCTC ACTGCAGCCT GCAACTGCTG CCTCCCGGGT
12051  TCAAGCGATT CTCCTGCCTC AGCCTCCTGA GTAGCTGGGA TTACAGGCAC
12101  CCGCCACCAC ACCCGGCTAA TTTTTGTATT TTTGTAGAGA CGGGGTTTCA
12151  CCATGTTGGC CAGGCCGGTC TCGAACTCCT GACCTCAGGT GATCCTCCCG
12201  CGTGAGCCGG CAGACTGTCA TTTCTCCATG GGCACCTCTG AATGTTGAGG
12251  CGGGTGATGG GTGGGAGGTT TAGATTGTGC TGCCTGCAGG GGCTCCCATC
12301  CCCATGCCGT GGATGCAGGA GGTGCCGTCT GGGTTCCTGC AACCACATTC
12351  AAGCCAATAC ACATTTACTG AGCGCTTGTT GTGTACCTCA TCCTGGGAGC
12401  TGTAGGCAGC AGCCCAGTGT TCCTTAGCTC CTAGAAATTC TAGGTCCCCT
12451  CTACATTCTT TGCATGTAGG CAGGATGACC TGGACCTGCA CTATCCAGTA
12501  CAGTAGCTGC TCACCACATG TGACTCTTTA AATTTAAATT AATTAAAATT
12551  AAACTCAATT CAGTTCCTCA GTTGCATTAG CCACATTTCA AGTACTCAGT
```

FIGURE 3, page 4 of 8

```
12601  AGACGCATGT GGCTGGTGGC TGAGGTATGG ATGGTGCAGA CGTAGAACCT
12651  TTCCATCATT GTAGAAAATT CTATCAGACA GCATTGCTCC GGCCACCTGC
12701  CAGGTGGTCC TCCGGGAGTG CTGGTGCGGA GTGCTGGTGC CGAGTGCTCA
12751  GAGTGGGTTC GGGTTCAGTC CCTGAACCCA AGCATCCTCT GCACCCAGAT
12801  CCTGCGGATC TGCACGCGGT ACACGCCCGA GCAGGACACC ATGACCTTCT
12851  CGGACGGGCT GACCCTGAAC CGGACCCAGA TGCACAACGC TGGCTTCGGC
12901  CCCCTCACCG ACCTGGTCTT TGCCTTCGCC AACCAGCTGC TGCCCCTGGA
12951  GATGGATGAT GCGGAGACGG GGCTGCTCAG CGCCATCTGC CTCATCTGCG
13001  GAGGTGGGCA GGGGGCCTGG GTCTGGGGGC TGGGCTGGGA CGGGGGTGCA
13051  GCCCTGGAGT CTCTTCCAGG GAGCTCTTTC AGGCCACCTC TGTTAGGTAT
13101  CTCTAGAGGG CAGGGTCTGG TCTGCAACTA CACAGCAAGG GGGCCATGTG
13151  GGGCCTGGAC TCCTGTTCCC GATTTCTGGG CAACACCCCT TCTAGGGAGG
13201  TTAAGAGTGA GGGTTTCAGG GTCGGACCAA CCAGGGTCAC CTCCTGGCCG
13251  ATGCATGACC CTGAGCAGGT TGCTGAACTT CTCTGGGCCT CCGTTTCTGT
13301  ACAGTGGGGG CGGTAACGGT CTCTAGCTCA TGAAGTTGAT GGGAGGATTA
13351  CGGTGGTAAC AGATACTGTG CAGGTGCCCA GAGCGAGCTC CAGTGCTTGT
13401  TAGTTGCTAT TTTATTGTTG TGATTTCTGC CATTTCATCT GGTTTCCAGA
13451  ATAACAGGGG GGAGTGGGAG CCTGCCTGGG AACCCTCTCC CTGCTTGAGG
13501  ATGGCACTGC CCATTTGGGG TCCCATCCCA CTAACTGGGC TCAGGGAGGG
13551  TTTGGGGCAC CCCCTCACCC TCAGCTCCCG TTGCTCCCTT TTAAGGGCCT
13601  CTGTACCCTG CGGCAGCAGA GACCCCATGC CCTGCCCTGT GTGGGGAGGC
13651  GCCTGCGAGC TGCCCTCCTC CATGGCCTGG GCAGGCACGC CCCCGGTGG
13701  CCGAGGCTGG GGGTGCAGCT GTGTTCCCAG CTGCTCAGGG GGTGGTTCTG
13751  CTTCCTCAGA CCGCCAGGAC CTGGAGCAGC CGGACCGGGT GGACATGCTG
13801  CAGGAGCCGC TGCTGGAGGC GCTAAAGGTC TACGTGCGGA AGCGGAGGCC
13851  CAGCCGCCCC CACATGTTCC CCAAGATGCT AATGAAGATT ACTGACCTGC
13901  GAAGCATCAG CGCCAAGGGT GAGGCTCACA GACCTGGAGG GGTACCGGCC
13951  CCCGACACCT GGCCCAGGCC CCACATCCA AGCCAGCACC CCATGTCTTT
14001  GTGCCAGGAC AATACACAC CTGTCCCCAT CTGTGTCTAG GCTGAGGTCC
14051  CCTAGTGACT CCACTTTGCC GAGGTGGCCC GCCTGTGTCA CCTTTGTGTG
14101  GTAGTTCAGA TCGTGGCTCT GGAACCAGAC ACGTGGGTGT GTGTCCTTGT
14151  GTGGGTCACT CAACAGCTCC TAGCTACAGT TTCCCTTCCG AGGGCGGGGA
14201  TAACATTCGT GTTTACAGAG GGGTCGGGAT GATCCCTAGC ACACAGCACA
14251  GGGGAAGGAA GGGCTTGGCG TCTAGCCCAG GCCGGCAGTC TGGCCCTGGA
14301  GCCGGAGTTC GGGACCACTT TGCCCCATTG CCACCAGCCT CTGGACCTGG
14351  GGGCTTAAGA GAGCTGGCTC GTGTCAAAGA ACTGAATCCC AAGAAAGATG
14401  CTAATATCAG CAGTATTGAT CTTCCCACCT CGAGCCAGGC TTGCTGGGGC
14451  TGGGGGTGGG AGGGCTGGCC CAGCGTGCTG ACCTCTGCCC CCTCCTTTCC
14501  TGCAGGGGCT GAGCGGGTGA TCACGCTGAA GATGGAGATC CCGGGCTCCA
14551  TGCCGCCTCT CATCCAGGAA ATGTTGGAGA ACTCAGAGGG CCTGGACACT
14601  CTGAGCGGAC AGCCGGGGGG TGGGGGGGCG GGACGGTGGT GGCCTTCTGC
14651  AGTAAAAAGT GCCCTGATGC CACCATTGCC GTAAAACTA ATGCCCAATT
14701  GTGATAAGGA GCTACCGGGG TACACACGGG GACTGGTTCA AATGGGGCAT
14751  CGCCGAAGCA TGTGATGCTA TGAACTTAAT CGGACTATTA TTCTGGTGGA
14801  TCCTCAAACC AGCATCGCAA CCTGGACACT CTTTTGCATG GTCGTTATTA
14851  TCTCCGGTAG ACTCCTTGCC TCCCTTTTAC ATAAAAAGGC CTCCCCCGAC
14901  AAAAAGGGTC AGTTCGATCC CCACTTTCGG TTCGGGAGCC TACCGTGTGC
14951  CAAAGGCCCT TAATCTCGAA AATATCCCAA TTACCTGATG TCGTGCGACG
15001  CCTAAAAATT CCCCGTGTTG CCACCACTGC TTGAAACCCC AAGCTTGGG
15051  TGTTAATCCC GAATTGGGGG CCCCCCGTGT NNNNNNNNNN NNNNNNNNNN
15101  NNNNNNNNNN NNNNNNNNNN NNNNNNNGG GCCCCCCGC CAGGCAGCTG
15151  TAGCCCCAGC CTCAGCCCCA GCTCCAACAG AAGCAGCCCG GCCACCCACT
15201  CCCCGTGACC GCCCACGCCA CATGGACACA GCCCTCGCCC TCCGCCCGG
15251  CTTTTCTCTG CCTTTCTACC GACCATGTGA CCCCGCACCA GCCCTGCCCC
15301  CACCTGCCCT CCCGGGCAGT ACTGGGGACC TTCCCTGGGG GACGGGAGG
15351  GAGGAGGCAG CGACTCCTTG GACAGAGGCC TGGGCCCTCA GTGGACTGCC
15401  TGCTCCCACA GCCTGGGCTG ACGTCAGAGG CCGAGGCCAG GAACTGAGTG
15451  AGGCCCTGG TCCTGGGTCT CAGGATGGGT CCTGGGGGCC TCGTGTTCAT
15501  CAAGACACCC CTCTGCCCAG CTCACCACAT CTTCATCACC AGCAAACGCC
15551  AGGACTTGGC TCCCCCATCC TCAGAACTCA CAAGCCATTG CTCCCCAGCT
15601  GGGGAACCTC AACCTCCCCC CTGCCTCGGT TGGTGACAGA GGGGGTGGGA
15651  CAGGGGCGGG GGGTTCCCCC TGTACATACC CTGCCATACC AACCCCAGGT
15701  ATTAATTCTC GCTGGTTTTG TTTTTATTTT AATTTTTTG TTTTGATTTT
```

FIGURE 3, page 5 of 8

```
15751  TTTAATAAGA ATTTTCATTT TAAGCACATT TATACTGAAG GAATTTGTGC
15801  TGTGTATTGG GGGGAGCTGG ATCCAGAGCT GGAGGGGGTG GGTCCGGGGG
15851  AGGGAGTGGC TCGGAAGGGG CCCCCACTCT CCTTTCATGT CCCTGTGCCC
15901  CCCAGTTCTC CTCCTCAGCC TTTTCCTCCT CAGTTTTCTC TTTAAAACTG
15951  TGAAGTACTA ACTTTCCAAG GCCTGCCTTC CCCTCCCTCC CACTGGAGAA
16001  GCCGCCAGCC CCTTTCTCCC TCTGCCTGAC CACTGGGTGT GGACGGTGTG
16051  GGGCAGCCCT GAAAGGACAG GCTCCTGGCC TTGGCACTTG CCTGCACCCA
16101  CCATGAGGCA TGGAGCAGGG CAGAGCAAGG GCCCCGGGAC AGAGTTTTCC
16151  CAGACCTGGC TCCTCGGCAG AGCTGCCTCC CGTCAGGGCC CACATCATCT
16201  AGGCTCCCCA GCCCCCACTG TGAAGGGGCT GGCCAGGGGC CCGAGCTGCC
16251  CCCACCCCCG GCCTCAGCCA CCAGCACCCC CATAGGGCCC CCAGACACCA
16301  CACACATGCG CGTGCGCACA CACACAAACA CACACACACT GGACAGTAGA
16351  TGGGCCGACA CACACTTGGC CCGAGTTCCT CCATTTCCCT GGCCTGCCCC
16401  CCACCCCCAA CCTGTCCCAC CCCCGTGCCC CCTCCTTACC CCGCAGGACG
16451  GGCCTACAGG GGGGTCTCCC CTCACCCCTG CACCCCCAGC TGGGGGAGCT
16501  GGCTCTGCCC CGACCTCCTT CACCAGGGGT TGGGGCCCCT TCCCCTGGAG
16551  CCCGTGGGTG CACCTGTTAC TGTTGGGCTT TCCACTGAGA TCTACTGGAT
16601  AAAGAATAAA GTTCTATTTA TTCTACACAT GCCTCCAGCC TTGCTGCCTC
16651  CACCCCCTCC TCTTGGCGTC TGGTCTGGGG GCTGGGATG GGTTTCGTCA
16701  TGTGCTCTGG GCCTGTGATG GCCAGGAATG AGCACTGGGG CCAAGGGGCT
16751  GGCCAGGGCA CCCTTCCAAG CTGCCTTCTG AGGCTTACCT TGTGCTGGGG
16801  TCTTTGGAGA TGCTGAGAAG GAGAAAGTCC TGCCCCTTGG GAAGCCCTCA
16851  GTCTGGGGAT CCACACTGCC CATGTCAAGG AGCCCAGTC TGGGAGTGGG
16901  AGAGAAGAGG AGGAAAGCTG CCCCCACCTT CAGGGAACCC CCAGTCTGAG
16951  GGAGGAAGCC GGAGCCACCC CTAGACATTT CTGGTCCTTG GGAAGCCTTC
```

FEATURES:

| | |
|---|---|
| Start: | 1684 |
| Exon: | 1684-1846 |
| Intron: | 1847-6808 |
| Exon: | 6809-6957 |
| Intron: | 6958-8277 |
| Exon: | 8278-8419 |
| Intron: | 8420-10406 |
| Exon: | 10407-10567 |
| Intron: | 10568-10827 |
| Exon: | 10828-11004 |
| Intron: | 11005-12798 |
| Exon: | 12799-13003 |
| Intron: | 13004-13759 |
| Exon: | 13760-13918 |
| Intron: | 13919-14505 |
| Exon: | 14506-14658 |
| Intron: | 14659-15143 |
| Exon: | 15144-15208 |
| Stop: | 15206 |

Map:
Bac Accession AC018629
Homo sapiens chromosome 17

FIGURE 3, page 6 of 8

SNP's:

| Position | Allele 1 | Allele 2 | Context |
|---|---|---|---|
| 4084 | C | G | GCCTCTCCCCGGGAGGAGGAAGGACGGTACAGAGGGCCCTACGCCCCCTCCCCAACCATCCCCAGG<br>GGCTGCGAGGGGAGCTGCGGAGGAGCGGGCGCCAGCTGGATTGGGAGGGGAGCCGCTGGCCGGGGG<br>CCCCGGCTGATTTCCTGCTGATCTCCTCCAGGAAACCGGCCCCTTGTGCGAGCCTGCGAACGGCTCG<br>GGGGCGTGGGGAATCCGGAGTGGAGCGCTCTGCGCCGCCCGCCCTGCCAGGATGGGGAGCGAGGGA<br>GGGGCACCCTGGCAGCGTCGGCGGGAGGGGACGCCT[C,G]<br>GCTTCCTGGGTCAGTTCCAGTCCTCTGTTGGGCGCTGGAACTTTGAGCTGAGAAGGTGTGGTCCTT<br>CTCTAGCCCGAGTCCTTCTGCAGGAAGAGGAGAGATTGGTGGGCTGGGCCTCTGGGGAGGGAGGTT<br>AGCAGGGATGGGCCAGGCCCGGGCAGTCCCTCCCCCGTTGGTGTCCCTCCCCACTCCACCTGTGTG<br>TGCAGGGAGTTATGGCCGTGTCCTAACTCTTGCAGAGGCTGTGAGGATTCCGGAGTTCCCCACACC<br>TCCGGCCTTGGTCCTTGTACCTCACCTCCTTGGACT |
| 6482 | G | A | ATCTCCCCCTATCTCAGGGAGACACCTCCTACTGTGCCCAGCATTTGTGACTCTTCTTTGCACCCC<br>CTGCCTTGGGTCCCTGGCCCTGGGATTGTTTGGGTGGAGGAGGGGCAGTGGCTGCTGGCAGAATGG<br>GGTGGAGGGGGGAGCGGAAGCAGAGGGGGCGGGGGAGTGGCCGGCTTTGAATATCCTGTTGACCCC<br>AGTTTCCTCTGCCCCCAGCTTATGTCCTCTTCCCTCCCTCCTCTTCAAGCGTTAACTCCTTCCTAA<br>CTCGGGGGGAGAACGGGGCCAGGCCGCCCAGGGGCA[G,A]<br>GAGCTTTAGAATCAGGGTGACCCCCACCCCTACTCCCCAAGCACAGTCACGGCACACATACAAATG<br>TGATGGTTTATCATTGTATCTTTGTGGTTTTGAAGGTGGGGGTCCTAGGAGTCCAGAGGAGTGATG<br>GGGTGCTGGAGGCTTCATTGGCAGCCTCCTGCCCTGAGTCTGGCTGGGGAGTCCCAGTTTTCTTAA<br>GACTTGAATCCTGCCAGCAGTGGTGAGGCTGGGAGAGGCTCTTAGGAGGGACGGTGAGGCAGGGTG<br>GAGCTTGGTACTAAGGATGGCGACCTAGGTCTCTAA |
| 8066 | C | G | TCTGTGATGGGTCGGTGCACACCTGTCTTGGTGAACTCACATCTTTCTGCCTTGCTCCTGAGTGCA<br>TGTGTGTGTTCGCCTCCATTTCTCTGGCCAGCCCGTGTATCTGCCTCCTGGCCTCTTCGGGCTTGT<br>CTTCTTTTCCTGTGTTCTGAGTTCAGGGGTGTGGGTTCCAGATCCCTGGCTGTTGCCCAGTTAGCC<br>CCATGTCTTCCTATTTCTGACTCACCAGCAGCCCTGAGGTCTTTTCCCTGGAAGGGAGGAGTCAGG<br>TGTGTGCTGTGGGTTGGGGGAAGACTCCTGCCCATC[C,G]<br>TGCAGTGTTGAGGCAGGTACTGGGATTCTCCTGAGGAGGATCCTTTTAGGTGAATCATTCTCCCCA<br>GCTTTTCTGGCCTGCTCAGGTAGGCGATGGGCAAACGCTTGGGGGCAGCAGCTGGCCTGGCCCTCC<br>TCCCCTAGACTGAGACCGTAGCCAGGCACTGCTCCCACTGTGGGTGTGGACAACCTGACTCCCTCC<br>CCTCCATACCCAGGGCTTCTTCCGCCGCAGCATCCAGAAGAACATGGTGTACACGTGTCACCGGGA<br>CAAGAACTGCATCATCAACAAGGTGACCCGGAACCG |
| 8699 | T | C | AAGTGGGCATGTCCAAGGAGTGTGAGTGCCATAGGGCAGGGGCCGAGTCCCGCCTCAGTTGGGGTC<br>TCAGATGCTCCTAAAGACCAAGGGAGCAGGGCTCTGTGGATGTTTGTGCACATGCATGAACACGCA<br>TGCCGTGGTGTGCGGGCTCACGGTTGAGGATGGTTTGTGTGTAGCTGCAAGGACCTGTTTGCGAGT<br>CTGGCTGGCTGTGTGTCCACGGGCAGGTCTGTGCTCCGGGACCGTGTATGTGTAACCATTCCTGTT<br>TCTGCACGTCTGGCTGTGTGTGCTTGCGTATGTGTG[T,C]<br>GTGTGTGCATGCTCCAGGATGGCTTTCTTCCAGGCCGTGCTTGGTTTTGGGGTGGGGCTCAGAGGC<br>ATAGGCAGTCCCTTCTGATTGTGAGTCTTAGGGGAGGGGCTTGAATTCTGAGGGGTGCTTGGCTGG<br>ACTTATGTGTGTATGGGGGGGTGGAAGGGCTGGCACAAGGATCCAAAAGCCATTGTCTAGTTAAGC<br>CTGGGATTCAGAGTTGGAAGAAAGAATTGGGACTTCTCAGATCCCAGAGGAAACGGGGTTTCCACT<br>TTGGGCTCAGCTGAGGCCTGATGGAGGGAGGGAGGG |
| 12897 | C | T | CAGTAGACGCATGTGGCTGGTGGCTGAGGTATGGATGGTGCAGACGTAGAACCTTTCCATCATTGT<br>AGAAAATTCTATCAGACAGCATTGCTCCGGCCACCTGCCAGGTGGTCCTCCGGGAGTGCTGGTGCG<br>GAGTGCTGGTGCCGAGTGCTCAGAGTGGGTTCGGGTTCAGTCCCTGAACCCAAGCATCCTCTGCAC<br>CCAGATCCTGCGGATCTGCACGCGGTACACGCCCGAGCAGGACACCATGACCTTCTCGGACGGGCT<br>GACCCTGAACCGGACCCAGATGCACAACGCTGGCTT[C,T]<br>GGCCCCCTCACCGACCTGGTCTTTGCCTTCGCCAACCAGCTGCTGCCCCTGGAGATGGATGATGCG<br>GAGACGGGGCTGCTCAGCGCCATCTGCCTCATCTGCGGAGGTGGGCAGGGGGCCTGGGTCTGGGGG<br>CTGGGCTGGGACGGGGGTGCAGCCCTGGAGTCTCTTCCAGGGAGCTCTTTCAGGCCACCTCTGTTA<br>GGTATCTCTAGAGGGCAGGGTCTGGTCTGCAACTACACAGCAAGGGGGCCATGTGGGGCCTGGACT<br>CCTGTTCCCGATTTCTGGGCAACACCCCTTCTAGGG |
| 14442 | C | T | TGTCCTTGTGTGGGTCACTCAACAGCTCCTAGCTACAGTTTCCCTTCCGAGGGCGGGGATAACATT<br>CGTGTTTACAGAGGGGTCGGGATGATCCCTAGCACACAGCACAGGGGAAGGAAGGGCTTGGCGTCT<br>AGCCCAGGCCGGCAGTCTGGCCCTGGAGCCGGAGTTCGGGACCACTTTGCCCCATTGCCACCAGCC<br>TCTGGACCTGGGGGCTTAAGAGAGCTGGCTCGTGTCAAAGAACTGAATCCCAAGAAAGATGCTAAT<br>ATCAGCAGTATTGATCTTCCCACCTCGAGCCAGGCT[C,T]<br>GCTGGGGCTGGGGGTGGGAGGGCTGGCCCAGCGTGCTGACCTCTGCCCCCTCCTTTCCTGCAGGGG<br>CTGAGCGGGTGATCACGCTGAAGATGGAGATCCCGGGCTCCATGCCGCCTCTCATCCAGGAAATGT<br>TGGAGAACTCAGAGGGCCTGGACACTCTGAGCGGACAGCCGGGGGGTGGGGGGCG |

FIGURE 3, page 7 of 8

| POSITION | Allele 1 | Allele 2 |        | Protein Position |   |   |
|----------|----------|----------|--------|------------------|---|---|
| 4084     | C        | G        | Intron |                  |   |   |
| 6482     | G        | A        | Intron |                  |   |   |
| 8066     | C        | G        | Intron |                  |   |   |
| 8699     | T        | C        | Intron |                  |   |   |
| 12897    | C        | T        | Exon   | 237              | F | L |
| 14442    | C        | T        | Intron |                  |   |   |

FIGURE 3, page 8 of 8

NUCLEIC ACID ENCODING RETINOIC ACID RECEPTOR

RELATED APPLICATIONS

The present application claims priority to provisional application U.S. Ser. No. 60/239,117, filed Oct. 11, 2000.

FIELD OF THE INVENTION

The present invention is in the field of nuclear hormone receptor proteins that are related to the retinoic acid receptor nuclear hormone receptor subfamily, recombinant DNA molecules, and protein production. The present invention specifically provides novel nuclear hormone receptor peptides and proteins and nucleic acid molecules encoding such peptide and protein molecules, all of which are useful in the development of human therapeutics and diagnostic compositions and methods.

BACKGROUND OF THE INVENTION

Nuclear Hormone Receptors

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the activation of gene transcription. Many of the transcription activation pathways are controlled by the action of intracellular receptors (IRs), such as members of the nuclear hormone receptor family of proteins and their ligands. The binding of a ligand to a nuclear hormone receptor serves to translate signals generated from a variety of cellular events.

Intracellular receptors (IRs) form a class of structurally related genetic regulators scientists have named "ligand dependent transcription factors." R. M. Evans, 240 Science, 889 (1988). Nuclear hormone receptors are a recognized subset of the IRs, including the progesterone receptor (PR), androgen receptor (AR), estrogen receptor (ER), glucocorticoid receptor (GR) and mineralocorticoid receptor (MR). Regulation of a gene by such factors requires both the IR itself and a corresponding ligand which has the ability to selectively bind to the IR in a way that alters gene transcription.

Ligands to the IRs can include low molecular weight native molecules, such as the hormones progesterone, estrogen and testosterone, as well as synthetic derivative compounds such as medroxyprogesterone acetate, diethylstilbesterol and 19-nortestosterone. These ligands, when present in the fluid surrounding a cell, pass through the outer cell membrane by passive diffusion and bind to specific IR proteins to create a ligand/receptor complex. This complex then translocates to the cell's nucleus, where it binds to a specific gene or genes present in the cell's DNA. Once bound to DNA, the complex modulates the production of the protein encoded by that gene. In this regard, a compound which binds and IR and mimics the effect of the native ligand is referred to as an "agonist", while a compound that inhibits the effect of the native ligand is called an "antagonist."

Ligands to the nuclear hormone receptors are known to play an important role in health of both women and men. For example, the native female ligand, progesterone, as well as synthetic analogues, such as norgestrel (18-homonorethisterone) and norethisterone (17.alpha.-ethinyl-19-nortestosterone), are used in birth control formulations, typically in combination with the female hormone estrogen or synthetic estrogen analogues, as effective modulators of both PR and ER. On the other hand, antagonists to PR are potentially useful in treating chronic disorders, such as certain hormone dependent cancers of the breast, ovaries, and uterus, and in treating non-malignant conditions such as uterine fibroids and endometriosis, a leading cause of infertility in women. Similarly, AR antagonists, such as cyproterone acetate and flutamide have proved useful in the treatment of hyperplasia and cancer of the prostate.

Nuclear hormone hormones, one sub-family of IRs, are potent modulators of transcriptional events that together regulate the complex processes associated with differentiation homeostasis and development. The mechanism of action of these molecules is related in that the effector molecule binds to a specific intracellular receptor. This binding alters the structure of the receptor, thus increasing its affinity for specific recognition sites within the regulatory region of target genes. In this way, the nuclear hormone directs a program of events that leads to a change in cell phenotype.

Nuclear hormone hormones, thyroid hormones and certain vitamins can regulate cellular differentiation morphogenesis and homeostasis by binding to specific intracellular receptor proteins. Ligand activated receptor complexes are capable of activating or repressing transcription of a specific set of target genes. Thus, the receptor proteins are capable of reprogramming cellular function at the genomic level in response to hormonal or vitamin signals.

Retinoic Acids and Retinoic Acid Receptors

The protein provided by the present invention is a novel retinoic acid receptor isoform; the new isoform provided herein is an ortholog of the rat retinoic acid receptor alpha 2. Consequently, the new retinoic acid receptor isoform provided by the present invention may be named human retinoic acid receptor alpha 2. As used herein, the term retinoic acid (RA) is synonymous with retinoid, and the term retinoic acid receptor is synonymous with retinoid receptor.

Retinoids, or vitamin A metabolites/derivatives, have been determined to play essential roles in many aspects of development, metabolism and reproduction in vertebrates (see, for example, The Retinoids, Second Edition, Sporn et al. (Raven Press, New York, 1994)). There are two classes of retinoid receptors: the retinoic acid receptors (RARs), which bind to both all-trans retinoic acid (atRA) and 9-cis retinoic acid (9cRA), and the retinoid X receptors (RXRs), which bind only to 9cRA. These receptors modulate ligand-dependent gene expression by interacting as RXR/RAR heterodimers or RXR homodimers on specific target gene DNA sequences known as hormone response elements. In addition to their role in retinoid signalling, RXRs also serve as heterodimeric partners of nuclear receptors for vitamin D, thyroid hormone, and peroxisome proliferators (reviewed by Mangelsdorf et al., at pages 319–349 of The Retinoids, Second Edition, Spom et al. (Raven Press, New York, 1994)).

A number of studies have demonstrated that retinoids are essential for normal growth, vision, tissue homeostasis, reproduction and overall survival (for reviews and references, See Sporn et al., The Retinoids, Vols. 1 and 2, Sporn et al., eds., Academic Press, Orlando, Fla. (1984)). For example, retinoids have been shown to be vital to the maintenance of skin homeostasis and barrier function in mammals (Fisher, G. J., and Voorhees, J. J., FASEB J. 10:1002–1013 (1996)). Retinoids are also apparently crucial during embryogenesis, since offspring of dams with vitamin A deficiency (VAD) exhibit a number of developmental defects (Wilson, J. G., et al., Am. J. Anat. 92:189–217 (1953); Morriss-Kay, G. M., and Sokolova, N., FASEB J. 10:961–968 (1996)). With the exceptions of those on vision (Wald, G., et al., Science 162:230–239 (1968)) and spermatogenesis in mammals (van Pelt, H. M. M., and De Rooij, D. G., Endocrinology 128:697–704 (1991)), most of the effects generated by VAD in animals and their fetuses can be prevented and/or reversed by retinoic acid (RA) administration (Wilson, J. G., et al., Am. J. Anat. 92:189–217 (1953); Thompson et al., Proc. Royal Soc. 159:510–535 (1964); Morriss-Kay, G. M., and Sokolova, N., FASEB J. 10:961–968 (1996)). The dramatic teratogenic effects of maternal RA administration on mammalian embryos (Shenefelt, R. E., Teratology 5, 103–108 (1972); Kessel, M., Development 115:487–501 (1992); Creech Kraft, J., In Retinoids in Normal Development and Teratogenesis, G. M. Morriss-Kay, ed., Oxford University Press, Oxford, UK, pp. 267–280 (1992)), and the marked effects of topical administration of retinoids on embryonic development of vertebrates and limb regeneration in amphibians (Mohanty-Hejmadi et al., Nature 355:352–353 (1992); Tabin, C. J., Cell 66:199–217 (1991)), have contributed to the notion that RA may have critical roles in morphogenesis and organogenesis.

Many synthetic structural analogues of all-trans retinoic acid or 9-cis-retinoic acid, commonly termed "retinoids", have been described in the literature to date. Some of these molecules are able to bind to, and specifically activate, the RARs or, on the other hand, the RXRs. Furthermore, some analogues are able to bind to, and activate a particular RAR receptor subtype (.alpha., .beta. or .gamma.). Finally, other analogues do not exhibit any particular selective activity with regard to these different receptors. In this respect, and by way of example, 9-cis-retinoic acid activates the RARs and the RXRs at one and the same time without any noteworthy selectivity for either of these receptors (nonspecific agonist ligand), whereas all-trans retinoic acid selectively activates the RARs (RAR-specific agonist ligand), with all subtypes being included. In a general manner, and qualitatively, a given substance (or ligand) is said to be specific for a given family of receptors (or, respectively, for a particular receptor of this family) when the said substance exhibits an affinity for all the receptors of this family (or, respectively, for the particular receptor of this family) which is stronger than that which it otherwise exhibits for all the receptors of any other family (or, respectively, for all the other receptors, of this same family or not).

The genetic activities of the RA signal are mediated through the two families of receptors—the RAR family and the RXR family—which belong to the superfamily of ligand-inducible transcriptional regulatory factors that include steroid/thyroid hormone and vitamin D3 receptors (for reviews see Leid et al., TIBS 17:427–433 (1992); Chambon, P., Semin. Cell Biol. 5:115–125 (1994); Chambon, P., FASEB J. 10:940–954 (1996); Giguere, V., Endocrinol. Rev. 15:61–79 (1994); Mangelsdorf, D. J., and Evans, R. M., Cell 83:841–850 (1995); Gronemeyer, H., and Laudet, V., Protein Profile 2:1173–1236 (1995)).

RARs are the critical factors in tissue differentiation and development They are up-regulated in rapidly dividing cells and tumors. RARs play an important role in lymphocyte activation. Synthetic antagonists of retinoic acid receptors can inhibit delayed type hypersensitivity (DTH). Growth factors and carotene regulate RXR expression levels. For example, granulocyte macrophage colony-stimulating factor induces retinoic acid receptors in myeloid leukemia cells.

Retinoic acid receptors can form heterodimers with other nuclear receptors. The protein provided by the present invention can be used as a probe to detect possible interactions in the two-hybrid assay. Synthetic peptides that mimic dimerization surface can disrupt intermolecular interactions between these receptors. RAR gene rearrangements are the primary causes of some types of leukemia and provide a convenient genetic marker for malignant cell lines. A number of retinoic acid derivatives are used in treatment of myelodysplastic disorders. They are designed to bind and activate RXRs. Beta-cotene can prevent skin tumor formation in mouse models. N-(4-hydroxyphenyl)retinarmide can delay onset of dysplasia in bronchi. Different chemopreventive drugs can be designed to target individual retinoic receptors. The sequences provided by the present invention may be used to design high affinity chemopreventive compounds.

Although both the RARs and RXRs respond to all-trans-retinoic acid in vivo, the receptors differ in several important aspects. First, the RARs and RXRs are significantly divergent in primary structure (e.g., the ligand binding domains of RAR.alpha and RXR.alpha. have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, in contrast to the RARS, which are generally not expressed at high levels in the visceral tissues, RXR.alpha. mRNA has been shown to be most abundant in the liver, kidney, lung, muscle and intestine. Finally, the RARs and RXRs have different target gene specificity. For example, response elements have recently been identified in the cellular retinal binding protein type II (CRBPII) and apolipoprotein A1 genes which confer responsiveness to RXR, but not RAR. Furthermore, RAR has also been recently shown to repress RXR-mediated activation through the CRBPII RXR response element (Manglesdorf et al., Cell, 66:555–61 (1991)). These data indicate that two retinoic acid responsive pathways are not simply redundant, but instead manifest a complex interplay. Recently, Heyman et al. (Cell, 68:397–406 (1992)) and Levin et al. (Nature, 355:359–61 (1992)) independently demonstrated that 9-cis-retinoic acid is a natural endogenous ligand for the RXRs. 9-cis-retinoic acid was shown to bind and transactivate the RXRs, as well as the RARs, and therefore appears to act as a "bifunctional" ligand.

RAR Receptors

Receptors belonging to the RAR family (RAR.alpha., .beta. and .gamma. and their isoforms) are activated by both all-trans- and 9-cis-RA (Leid et al., TIBS 17:427–433 (1992); Chambon, P., Semin. Cell Biol. 5:115–125 (1994); Dolle, P., et al., Mech. Dev. 45:91–104 (1994); Chambon, P., FASEB J. 10:940–954 (1996)). Within a given species, the DNA binding (C) and the ligand binding (E) domains of the three RAR types are highly similar, whereas the C-terminal domain F and the middle domain D exhibit no or little similarity. The amino acid sequences of the three RAR types are also notably different in their B regions, and their main isoforms (.alpha.1 and .alpha.2, .beta.1 to .beta.4, and .gamma.1 and .gamma.2) further differ in their N-terminal A regions (Leid et al., TIBS 17:427–433 (1992)). Amino acid sequence comparisons have revealed that the interspecies conservation of a given RAR type is greater than the similarity found between the three RAR types within a given species (Leid et al., TIBS 17:427–433 (1992)). This interspecies conservation is particularly striking in the N-terminal A regions of the various RAR.alpha., .beta. and .gamma. isoforms, whose A region amino acid sequences are quite divergent. Taken together with the distinct spatio-temporal expression patterns observed for the transcripts of each RAR and RXR type in the developing embryo and in various adult mouse tissues (Zelent, A., et al., Nature 339:714–717 (1989); Dolle, P., et al., Nature 342:702–705 (1989); Dolleet al., Development 110:1133–1151 (1990); Ruberte et al., Development 108:213–222 (1990); Ruberte et al., Development 111:45–60 (1991); Mangelsdorf et al., Genes & Dev. 6:329–344 (1992)), this interspecies conservation has suggested that each RAR type (and isoform) may perform unique functions. This hypothesis is further supported by the finding that the various RAR isoforms contain two transcriptional activation functions (AFs) located in the N-terminal A/B region (AF-1) and in the C-terminal E region (AF-2), which can synergistically, and to some extent differentially, activate various RA-responsive promoters (Leid et al., TIBS 17:427433 (1992); Nagpal, S., et al., Cell 70:1007–1019 (1992); Nagpal, S., et al., EMBO J. 12:2349–2360 (1993)).

RXR Receptors

Unlike the RARs, members of the retinoid X receptor family (RXR.alpha., .beta. and .gamma.) are activated exclusively by 9-cis-RA (Chambon, P., FASEB J. 10:940–954 (1996); Chambon, P., Semin. Cell Biol. 5:115–125 (1994); Dolle, P., et al., Mech. Dev. 45:91–104 (1994); Linney, E., Current Topics in Dev. Biol. 27:309–350 (1992); Leid et al., TIBS 17:427–433 (1992); Kastner et al., in Vitamin A in Health and Disease, R. Blomhoff, ed., Marcel Dekker, New York (1993)). However, the RXRs characterized to date are similar to the RARs in that the different RXR types also differ markedly in their N-terminal A/B regions (Leid et al., TIBS 17:427–433 (1992); Leid et al., Cell 68:377–395 (1992); Mangelsdorf et al., Genes and Dev. 6:329–344 (1992)), and contain the same transcriptional activation functions in their N-terminal A/B region and C-terminal E region (Leid et al., TIBS 17:427–433 (1992); Nagpal, S., et al., Cell 70:1007–1019 (1992); Nagpal, S., et al., EMBO J. 12:2349–2360(1993)).

RXR.alpha. and RXR.beta. have a widespread (possibly ubiquitous) expression pattern during mouse development and in the adult animal, being found in all fetal and adult tissues thus far examined (Mangelsdorf, D. J., et al., Genes & Devel. 6:329–344 (1992); Dolle, P., et al., Mech. Devel. 45:91–104 (1994); Nagata, T., et al., Gene 142:183–189 (1994)). RXR.gamma. transcripts, however, appear to have a more restricted distribution, being expressed in developing skeletal muscle in the embryo (where their expression persists throughout life), in the heart (after birth), in sensory epithelia of the visual and auditory systems, in specific structures of the central nervous system, and in tissues involved in thyroid hormone homeostasis, e.g., the thyroid gland and thyrotrope cells in the pituitary (Mangelsdorf, D. J., et al., Genes & Devel. 6:329–344 (1992); Dolle, P., et al., Mech. Devel. 45:91–104 (1994); Sugawara, A., et al., Endocrinology 136:1766–1774 (1995); Liu, Q., and Linney, E., Mol. Endocrinol. 7:651–658 (1993)).

It is currently unclear whether all the molecular properties of RXRs characterized in vitro are relevant for their physiological functions in vivo. In particular, it is unknown under what conditions these receptors act as 9-cis-RA-dependent transcriptional regulators (Chambon, P., Semin. Cell Biol. 5:115–125 (1994)). The knock-outs of RXR.alpha. and RXR.beta. in the mouse have provided some insight into the physiological functions of these receptors. For example, the ocular and cardiac malformations observed in RXR.alpha ... sup.-/- fetuses (Kastner, P., et al., Cell 78:987–1003 (1994); Sucov, H. M., et al., Genes & Devel. 8:1007–1018 (1994)) are similar to those found in the fetal VAD syndrome, thus suggesting an important function of RXR.alpha. in the transduction of a retinoid signal during development. The involvement of RXRs in retinoid signaling is further supported by studies of compound RXR.alpha./RAR mutants, which reveal defects that are either absent or less severe in the single mutants (Kastner, P., et al., Cell 78:987–1003 (1994); Kastner, P., et al., Cell 83:859–869 (1995)). Interestingly, however, knockout of RXR.gamma. in the mouse induces no overt deleterious effects, and RXR.gamma ... sup.-/- homozygotes which are also RXR.alpha ... sup.-/- or RXR.beta ... sup.-/- exhibit no additional abnormalities beyond those seen in RXR.alpha ... sup.-/-, RXR.beta ... sup.-/- and fetal VAD syndrome fetuses (Krezel, W., et al., Proc. Natl. Acad. Sci. USA 93(17):9010–9014 (1996)), suggesting that RXR.gamma., despite its highly tissue-specific expression pattern in the developing embryo, is dispensable for embryonic development and postnatal life in the mouse. The observation that live-born RXR.gamma ... sup.-/-/ RXR.beta ... sup.-/-/RXR.alpha ... sup.-/- mutants can grow to reach adult age (Krezel et al., Proc. Natl. Acad. Sci. USA 93(17):9010–9014 (1996)) indicates that a single RXR.alpha. allele is sufficient to carry out all of the vital developmental and postnatal functions of the RXR family of receptors, particularly all of the developmental functions which depend on RARs and may require RXR partnership (Dolle, P., et al., Mech. Dev. 45:91–104 (1994); Kastner, P., et al., Cell 83:859–869 (1995)). Furthermore, the finding that RXR.alpha ... sup.-/-/RXR.gamma ... sup.-/- double mutant embryos are not more affected than are single RXR.alpha ... sup.-/- mutants (Krezel et al., Proc. Natl. Acad. Sci. USA 93(17):9010–9014 (1996)) clearly shows that RXR.beta.alone can also perform some of these functions. Therefore, the fact that RXR.alpha. alone and, to a certain extent RXR.beta. alone, are sufficient for the completion of a number of developmental RXR functions, clearly indicates the existence of a large degree of functional redundancy amongst RXRs. In this respect, the RXR situation is different from that of RARs, since all of types of RAR double mutants displayed much broader sets of defects than single mutants Rowe, A., et al., Develop. 111:771–778 (1991); Lohnes, D., et al., Develop. 120:2723–2748 (1994); Mendelsohn, C., Develop. 120:2749–2771 (1994)).

Retinoid Binding to RAR and RXR Receptors

The crystal structures of the ligand-binding domains (LBDs) of the RARs and RXRs have recently been elucidated (Bourget, W., et al., Nature 375:377–382 (1995); Renaud, J. P., et al., Nature 378:681–689 (1995); Wurtz, J. M., et al., Nature Struct. Biol. 3:87–94 (1996)). Among the various RAR types, substantial amino acid sequence identity is observed in these domains: comparison of the LBDs of RAR.alpha., RAR.beta. and RAR.gamma. indicates that only three amino acid residues are variable in the ligand-binding pocket of these receptors. These residues apparently account for the fact that the various RAR types exhibit some selectivity in binding certain synthetic retinoids (Chen, J.-Y., et al., EMBO J. 14(6):1187–1197 (1995); Renaud, J. P., et al., Nature 378:681–689 (1995)), and consideration of these divergent residues can be used to design RAR type-specific synthetic retinoids which may be agonistic or antagonistic (Chambon, P., FASEB J. 10:940–954 (1996)). This design approach may be extendable generally to other nuclear receptors, such as thyroid receptor .alpha. (Wagner, R. L., et al., Nature 378:690–697 (1995)), the ligand-binding pockets of which may chemically and structurally resemble those of the RARs (Chambon, P., FASEB J. 10:940–954 (1996)). Conversely, molecular modeling of the ligand-binding pocket of the RXRs demonstrates that there are no overt differences in amino acid composition between RXR.alpha., RXR.beta. and RXR.gamma. (Bourguet, W., et al., Nature 375:377–382 (1995); Wurtz, J. M., et al., Nature Struct. Biol. 3:87–94 (1996)), suggesting that design of type-specific synthetic ligands for the RXRs may be more difficult than for the RARs (Chambon, P., FASEB J. 10:940–954 (1996)).

Retinoid Signaling Through RAR:RXR Heterodimers

Nuclear receptors (NRs) are members of a superfamily of ligand-inducible transcriptional regulatory factors that include receptors for steroid hormones, thyroid hormones, vitamin D3 and retinoids (Leid, M., et al., Trends Biochem. Sci. 17:427433 (1992); Leid, M., et al., Cell 68:377–395 (1992); and Linney, E. Curr. Top. Dev. Biol., 27:309–350 (1992)). NRs exhibit a modular structure which reflects the existence of several autonomous functional domains. Based on amino acid sequence similarity between the chicken estrogen receptor, the human estrogen and glucocorticoid receptors, and the v-erb-A oncogene (Krust, A., et al., EMBO J. 5:891–897 (1986)), defined six regions—A, B, C, D, E and F—which display different degrees of evolutionary conservation amongst various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1 and AF-2 of steroid receptors exhibit differential transcriptional activation properties which appear to be both cell type and promoter context specific (Gronemeyer, H. Annu. Rev. Genet. 25:89–123 (1991)).

As described above, the all-trans (T-RA) and 9-cis (9C-RA) retinoic acid signals are transduced by two families of nuclear receptors, RAR .alpha., .beta. and .gamma. (and their isoforms) are activated by both T-RA and 9C-RA, whereas RXR .alpha., .beta. and .gamma. are exclusively activated by 9C-RA (Allenby, G. et al., Proc. Natl. Acad. Sci. USA 90:30–34 (1993)). The three RAR types differ in their B regions, and their main isoforms (.alpha.1 and .alpha.2, .beta. 1–4, and .gamma.1 and .gamma.2) have different N-terminal A regions (Leid, M. et al., Trends Biochem. Sci. 17:427–433 (1992)). Similarly, the RXR types differ in their A/B regions (Mangelsdorf, D. J. et al., Genes Dev. 6:329–344 (1992)).

The E-region of RARs and RXRs has also been shown to contain a dimerization interface (Yu, V. C. et al., Curr. Opin. Biotechnol. 3:597–602 (1992)). Most interestingly, it was demonstrated that RAR/RXR heterodimers bind much more efficiently in vitro than homodimers of either receptor to a number of RA response elements (RAREs) (Yu, V. C. et al., Cell 67:1251–1266 (1991); Berrodin, T. J. et al., Mol. Endocrinol 6:1468–1478 (1992); Bugge, T. H. et al., EMBO J. 11:1409–1418 (1992); Hall, R. K. et al., Mol. Cell. Biol. 12: 5527–5535 (1992); Hallenbeck P. L. et al., Proc. Natl. Acad. Sci. USA 89:5572–5576 (1992); Husmann, M. et al., Biochem. Biophys. Res. Commun. 187:1558–1564 (1992); Kliewer, S. A. et al., Nature 355:446–449 (1992); Leid, M. et al., Cell 68:377–395 (1992); Marks, M. S. et al., EMBO J. 11:1419–1435 (1992); Zhang, X. K. et al., Nature 355:441–446 (1992)). RAR and RXR heterodimers are also preferentially formed in solution in vitro (Yu, V. C. et al., Cell 67:1251–1266 (1991); Leid, M. et al., Cell 68:377–395 (1992); Marks, M. S. et al., EMBO J. 11:1419–1435 (1992)), although the addition of 9C-RA appears to enhance the formation of RXR homodimers in vitro (Lehman, J. M. et al., Science 258:1944–1946 (1992); Zhang, X. K. et al., Nature 358:587–591 (1992b)).

It has been shown that activation of RA-responsive promoters likely occurs through RAR:RXR heterodimers rather than through homodimers (Yu, V. C. et al., Cell 67:1251–1266 (1991); Leid et al., Cell 68:377–395 (1992b); Durand et al., Cell 71:73–85 (1992); Nagpal et al., Cell 70:1007–1019 (1992); Zhang, X. K., et al., Nature 355, 441–446 (1992); Kliewer et al., Nature 355:446–449 (1992); Bugge et al., EMBO J. 11: 1409–1418 (1992); Marks et al., EMBO J. 11:1419–1435 (1992); Yu, V. C. et al., Cur. Op. Biotech. 3:597–602 (1992); Leid et al., TIBS 17:427–433 (1992); Laudet and Stehelin, Curr. Biol. 2:293–295 (1992); Green, S., Nature 361:590–591 (1993)). The RXR portion of these heterodimers has been proposed to be silent in retinoid-induced signaling (Kurokawa, R., et al., Nature 371:528–531 (1994); Forman, B. M., et al., Cell 81:541–550 (1995); Mangelsdorf, D. J., and Evans, R. M., Cell 83:835–850 (1995)), although conflicting results have been reported on this issue (Apfel, C. M., et al., J. Biol. Chem. 270(51):30765–30772 (1995); see Chambon, P., FASEB J. 10:940–954 (1996) for review). Although the results of these studies strongly suggest that RAR/RXR heterodimers are indeed fractional units that transduce the RA signal in vivo, it is unclear whether all of the suggested heterodimeric combinations occur in vivo (Chambon, P., Semin. Cell Biol. 5:115–125 (1994)). Thus, the basis for the highly pleiotropic effect of retinoids may reside, at least in part, in the control of different subsets of retinoid-responsive promoters by cell-specifically expressed heterodimeric combinations of RAR:RXR types (and isoforms), whose activity may be in turn regulated by cell-specific levels of all-trans- and 9-cis-RA (Leid et al., TIBS 17:427–433 (1992)).

The RXR receptors may also be involved in RA-independent signaling. For example, the observation of aberrant lipid metabolism in the Sertoli cells of RXR.beta . . . sup.–/– mutant animals suggests that functional interactions may also occur between RXR.beta. and the peroxisomal proliferator-activated receptor signaling pathway (WO 94/26100; Kastner, P., et al., Genes & Devel. 10:80–92 (1996)).

For a further review of retinoic acid receptors, see: Shimizu et al., Cancer Res 2000 August 15;60(16):4544–9; Ponnamperuma et al., Nutr Cancer 2000;37(1):82–8; Yoshimura et al., J Med Chem 2000 Jul 27;43(15):2929–37; Kurie et al., Clin Cancer Res 2000 Aug;6(8):2973–9; Lee et al., J Biol Chem 2000 Aug 17; and Sainty et al., Blood 2000 Aug 15;96(4):1287–96.

The discovery of a new human nuclear hormone receptor proteins and the polynucleotides encoding it satisfies a need in the art by providing new compositions which are useful in the diagnosis, prevention and treatment of biological processes associated with abnormal or unwanted protein gene activation.

SUMMARY OF THE INVENTION

The present invention is based in part on the identification of amino acid sequences of human nuclear hormone receptor peptides and proteins that are related to the retinoic acid receptor nuclear hormone receptor subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate nuclear hormone receptor activity in cells and tissues that express the nuclear hormone receptor. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen.

DESCRIPTION OF THE FIGURE SHEETS

FIG. 1 provides the nucleotide sequence of a cDNA molecule or transcript sequence that encodes the nuclear hormone receptor protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen.

FIG. 2 provides the predicted amino acid sequence of the nuclear hormone receptor of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the nuclear hormone receptor protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, known SNP variations include C4084G, G6482A, C8066G, T8699C, C1289T, and C14442T.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a nuclear hormone receptor protein or part of a nuclear hormone receptor protein and are related to the retinoic acid receptor nuclear hormone receptor subfamily. Utilizing these sequences, additional genomic sequences were assembled and transcript and/or cDNA sequences were isolated and characterized. Based on this analysis, the present invention provides amino acid sequences of human nuclear hormone receptor peptides and proteins that are related to the retinoic acid receptor nuclear hormone receptor subfamily, nucleic acid sequences in the form of transcript sequences, cDNA sequences and/or genomic sequences that encode these nuclear hormone receptor peptides and proteins, nucleic acid variation (allelic information), tissue distribution of expression, and information about the closest art known protein/peptide/domain that has structural or sequence homology to the nuclear hormone receptor of the present invention.

In addition to being previously unknown, the peptides that are provided in the present invention are selected based on their ability to be used for the development of commercially important products and services. Specifically, the present peptides are selected based on homology and/or structural relatedness to known nuclear hormone receptor proteins of the retinoic acid receptor nuclear hormone receptor subfamily and the expression pattern observed. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known retinoic acid receptor family or subfamily of nuclear hormone receptor proteins.

Specific Embodiments

Peptide Molecules

The present invention provides nucleic acid sequences that encode protein molecules that have been identified as being members of the nuclear hormone receptor family of proteins and are related to the retinoic acid receptor nuclear hormone receptor subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the nuclear hormone receptor peptides of the present invention, nuclear hormone receptor peptides, or peptides/proteins of the present invention.

The present invention provides isolated peptide and protein molecules that consist of, consist essentially of, or comprise the amino acid sequences of the nuclear hormone receptor peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the nuclear hormone receptor peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated nuclear hormone receptor peptide can be purified from cells that naturally express it, purified from cells that have been altered to express it (recombinant), or synthesized using known protein synthesis methods. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. For example, a nucleic acid molecule encoding the nuclear hormone receptor peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the nuclear hormone receptor peptides of the present invention are the naturally occurring mature proteins. A brief description of how various types of these proteins can be made/isolated is provided below.

The nuclear hormone receptor peptides of the present invention can be attached to heterologous sequences to form chimeric or fusion proteins. Such chimeric and fusion proteins comprise a nuclear hormone receptor peptide operatively linked to a heterologous protein having an amino acid sequence not substantially homologous to the nuclear hormone receptor peptide. "Operatively linked" indicates that the nuclear hormone receptor peptide and the heterologous protein are fused in-frame. The heterologous protein can be fused to the N-terminus or C-terminus of the nuclear hormone receptor peptide.

In some uses, the fusion protein does not affect the activity of the nuclear hormone receptor peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant nuclear hormone receptor peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A nuclear hormone receptor peptide-encoding nucleic acid can be cloned into such an expression vector such that the fusion moiety is linked in-frame to the nuclear hormone receptor peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the nuclear hormone receptor peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the nuclear hormone receptor peptides of the present invention as well as being encoded by the same genetic locus as the nuclear hormone receptor peptide provided herein. As indicated by the data presented in FIG. 3, the nuclear hormone receptor of the present invention was determined to be located on a Bacteria Artificial Chromosome ("BAC"), Bac Accession AC018629, which is known to be on chromosome 17.

Allelic variants of a nuclear hormone receptor peptide can readily be identified as being a human protein having a high degree (significant) of sequence homology/identity to at least a portion of the nuclear hormone receptor peptide as well as being encoded by the same genetic locus as the nuclear hormone receptor peptide provided herein. Genetic locus can readily be determined based on the genomic information provided in FIG. 3, such as the genomic sequence mapped to the reference human. As indicated by the data presented in FIG. 3, the nuclear hormone receptor of the present invention was determined to be located on a Bacteria Artificial Chromosome ('BAC'), Bac Accession AC018629, which is known to be on chromosome 17. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a nuclear hormone receptor peptide encoding nucleic acid molecule under stringent conditions as more fully described below.

FIG. 3 provides SNP information that has been found in a gene encoding the nuclear hormone proteins of the present invention. The following variations were seen: C4084G, G6482A, C8066G, T8699C, C12897T, and C14442T. The changes in the amino acid that these SNPs cause can readily be determined using the universal genetic code and the protein sequence provided in FIG. 2 as a base.

Paralogs of a nuclear hormone receptor peptide can readily be identified as having some degree of significant sequence homology/identity to at least a portion of the nuclear hormone receptor peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a nuclear hormone receptor peptide encoding nucleic acid molecule under moderate to stringent conditions as more fully described below.

Orthologs of a nuclear hormone receptor peptide can readily be identified as having some degree of significant sequence homology/identity to at least a portion of the nuclear hormone receptor peptide as well as being encoded by a gene from another organism. Preferred orthologs will be isolated from mammals, preferably primates, for the development of human therapeutic targets and agents. Such orthologs will be encoded by a nucleic acid sequence that will hybridize to a nuclear hormone receptor peptide encoding nucleic acid molecule under moderate to stringent conditions, as more fully described below, depending on the degree of relatedness of the two organisms yielding the proteins.

Non-naturally occurring variants of the nuclear hormone receptor peptides of the present invention can readily be generated using recombinant techniques. Such variants include, but are not limited to deletions, additions and substitutions in the amino acid sequence of the nuclear hormone receptor peptide. For example, one class of substitutions are conserved amino acid substitution. Such substitutions are those that substitute a given amino acid in a nuclear hormone receptor peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306–1310 (1990).

Variant nuclear hormone receptor peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)), particularly using the results provided in FIG. 2. The latter procedure introduces single alanine mutations at every residue in the molecule. The resulting mutant molecules are then tested for biological activity such as nuclear hormone receptor activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899–904 (1992); de Vos et al, Science 255:306–312 (1992)).

The present invention further provides fragments of the nuclear hormone receptor peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a nuclear hormone receptor peptide. Such fragments can be chosen based on the ability to retain one or more of the biological activities of the nuclear hormone receptor peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the nuclear hormone receptor peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in nuclear hormone receptor peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W. H. Freeman and Company, New York (1993). Many detailed reviews are available on this subject, such as by Wold, F., Posttranslational Covalent Modification of proteins, B. C. Johnson, Ed., Academic Press, New York 1–12 (1983); Seifter et al. (Meth. Enzymol. 182: 626–646 (1990)) and Rattan et al. (Ann N.Y. Acad. Sci. 663:48–62 (1992)).

Accordingly, the nuclear hormone receptor peptides of the present invention also encompass derivatives or analogs in which a substituted amino acid residue is not one encoded by the genetic code, in which a substituent group is included, in which the mature nuclear hormone receptor peptide is fused with another compound, such as a compound to increase the half-life of the nuclear hormone receptor peptide (for example, polyethylene glycol), or in which the additional amino acids are fused to the mature nuclear hormone receptor peptide, such as a leader or secretory sequence or a sequence for purification of the mature nuclear hormone receptor peptide or a pro-protein sequence.

Protein/Peptide Uses

The proteins of the present invention can be used in substantial and specific assays related to the fractional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a nuclear hormone receptor-effector protein interaction or nuclear hormone receptor-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, nuclear hormone receptors isolated from humans and their human/mammalian orthologs serve as targets for identifying agents for use in mammalian therapeutic applications, e.g. a human drug, particularly in modulating a biological or pathological response in a cell or tissue that expresses the nuclear hormone receptor. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue. A large percentage of pharmaceutical agents are being developed that modulate the activity of nuclear hormone receptor proteins, particularly members of the retinoic acid receptor subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Such uses can readily be determined using the information provided herein, that which is known in the art, and routine experimentation.

The proteins of the present invention (including variants and fragments that may have been disclosed prior to the present invention) are useful for biological assays related to nuclear hormone receptors that are related to members of the retinoic acid receptor subfamily. Such assays involve any of the known nuclear hormone receptor functions or activities or properties useful for diagnosis and treatment of nuclear hormone receptor-related conditions that are specific for the subfamily of nuclear hormone receptors that the one of the present invention belongs to, particularly in cells and tissues that express the nuclear hormone receptor. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue.

The proteins of the present invention are also useful in drug screening assays, in cell-based or cell-free systems. Cell-based systems can be native, i.e., cells that normally express the nuclear hormone receptor, as a biopsy or expanded in cell culture. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. In an alternate embodiment, cell-based assays involve recombinant host cells expressing the nuclear hormone receptor protein.

The polypeptides can be used to identify compounds that modulate nuclear hormone receptor activity of the protein in its natural state or an altered form that causes a specific disease or pathology associated with the nuclear hormone receptor. Both the nuclear hormone receptors of the present invention and appropriate variants and fragments can be used in high-throughput screens to assay candidate compounds for the ability to bind to the nuclear hormone receptor. These compounds can be further screened against a functional nuclear hormone receptor to determine the effect of the compound on the nuclear hormone receptor activity. Further, these compounds can be tested in animal or invertebrate systems to determine activity/effectiveness. Compounds can be identified that activate (agonist) or inactivate (antagonist) the nuclear hormone receptor to a desired degree.

Further, the proteins of the present invention can be used to screen a compound for the ability to stimulate or inhibit interaction between the nuclear hormone receptor protein and a molecule that normally interacts with the nuclear hormone receptor protein, e.g. a substrate or a component of the signal pathway that the nuclear hormone receptor protein normally interacts (for example, another nuclear hormone receptor). Such assays typically include the steps of combining the nuclear hormone receptor protein with a candidate compound under conditions that allow the nuclear hormone receptor protein, or fragment, to interact with the target molecule, and to detect the formation of a complex between the protein and the target or to detect the biochemical consequence of the interaction with the nuclear hormone receptor protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Song yang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant nuclear hormone receptors or appropriate fragments containing mutations that affect nuclear hormone receptor function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) nuclear hormone receptor activity. The assays typically involve an assay of events in the signal transduction pathway that indicate nuclear hormone receptor activity. Thus, the phosphorylation of a substrate, activation of a protein, a change in the expression of genes that are up or down-regulated in response to the nuclear hormone receptor protein dependent signal cascade can be assayed.

Any of the biological or biochemical functions mediated by the nuclear hormone receptor can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the nuclear hormone receptor can be assayed. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue.

Binding and/or activating compounds can also be screened by using chimeric nuclear hormone receptor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native nuclear hormone receptor. Accordingly, a different set of signal transduction components is available as an end-point assay for activation. This allows for assays to be performed in other than the specific host cell from which the nuclear hormone receptor is derived.

The proteins of the present invention are also useful in competition binding assays in methods designed to discover compounds that interact with the nuclear hormone receptor (e.g. binding partners and/or ligands). Thus, a compound is exposed to a nuclear hormone receptor polypeptide under conditions that allow the compound to bind or to otherwise interact with the polypeptide. Soluble nuclear hormone receptor polypeptide is also added to the mixture. If the test compound interacts with the soluble nuclear hormone receptor polypeptide, it decreases the amount of complex formed or activity from the nuclear hormone receptor target. This type of assay is particularly useful in cases in which compounds are sought that interact with specific regions of the nuclear hormone receptor. Thus, the soluble polypeptide that competes with the target nuclear hormone receptor region is designed to contain peptide sequences corresponding to the region of interest.

To perform cell free drug screening assays, it is sometimes desirable to immobilize either the nuclear hormone receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of nuclear hormone receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a nuclear hormone receptor-binding protein and a candidate compound are incubated in the nuclear hormone receptor protein-presenting wells and the amount of complex trapped in the well can be quantitated. Methods for detecting such complexes, in addition to those described above for the GST-immobilized complexes, include immunodetection of complexes using antibodies reactive with the nuclear hormone receptor protein target molecule, or which are reactive with nuclear hormone receptor protein and compete with the target molecule, as well as enzyme-linked assays which rely on detecting an enzymatic activity associated with the target molecule.

Agents that modulate one of the nuclear hormone receptors of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of nuclear hormone receptor protein activity identified according to these drug screening assays can be used to treat a subject with a disorder mediated by the nuclear hormone receptor pathway, by treating cells or tissues that express the nuclear hormone receptor. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. These methods of treatment include the steps of administering a modulator of nuclear hormone receptor activity in a pharmaceutical composition to a subject in need of such treatment, the modulator being identified as described herein.

In yet another aspect of the invention, the nuclear hormone receptor proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the nuclear hormone receptor and are involved in nuclear hormone receptor activity. Such nuclear hormone receptor-binding proteins are also likely to be involved in the propagation of signals by the nuclear hormone receptor proteins or nuclear hormone receptor targets as, for example, downstream elements of a nuclear hormone receptor-mediated signaling pathway. Alternatively, such nuclear hormone receptor-binding proteins are likely to be nuclear hormone receptor inhibitors.

The two-hybrid system is based on the modular nature of most transcription factors, which consist of separable DNA-binding and activation domains. Briefly, the assay utilizes two different DNA constructs. In one construct, the gene that codes for a nuclear hormone receptor protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a nuclear hormone receptor-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the nuclear hormone receptor protein.

This invention further pertains to novel agents identified by the above-described screening assays. Accordingly, it is within the scope of this invention to further use an agent identified as described herein in an appropriate animal model. For example, an agent identified as described herein (e.g., a nuclear hormone receptor-modulating agent, an antisense nuclear hormone receptor nucleic acid molecule, a nuclear hormone receptor-specific antibody, or a nuclear hormone receptor-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The nuclear hormone receptor proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. The method involves contacting a biological sample with a compound capable of interacting with the nuclear hormone receptor protein such that the interaction can be detected. Such an assay can be provided in a single detection formal or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered nuclear hormone receptor activity in cell-based or cell-free assay, alteration in a substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the nuclear hormone receptor protein in which one or more of the nuclear hormone receptor functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and nuclear hormone receptor activation. Accordingly, substrate dosage would necessarily be modified to maximize the therapeutic effect within a given population containing a polymorphism.

As an alternative to genotyping, specific polymorphic peptides could be identified.

The peptides are also useful for treating a disorder characterized by an absence of, inappropriate, or unwanted expression of the protein. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Accordingly, methods for treatment include the use of the nuclear hormone receptor protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the nuclear hormone receptor proteins. Antibodies can be prepared from any region of the peptide as described herein. However, preferred regions will include those involved in function/activity and/or nuclear hormone receptor/binding partner interaction. FIG. 2 can be used to identify particularly important regions while sequence alignment can be used to identify conserved and unique sequence fragments.

An antigenic fragrant will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, $\epsilon$-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Thus, where a specific protein has been correlated with expression in a specific tissue, antibodies that are specific for this protein can be used to identify a tissue type.

The antibodies are also useful for inhibiting protein function, for example, blocking the binding of the nuclear hormone receptor peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a nuclear hormone receptor peptide or protein of the present invention (cDNA, transcript and genomic sequence). Such nucleic acid molecules will consist of, consist essentially of, or comprise a nucleotide sequence that encodes one of the nuclear hormone receptor peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the nuclear hormone receptor peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the nuclear hormone receptor proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the nuclear hormone receptor of the present invention was determined to be located on a Bacteria Artificial Chromosome ("BAC"), Bac Accession AC018629, which is known to be on chromosome 17.

FIG. 3 provides SNP information that has been found in a gene encoding the nuclear hormone proteins of the present invention. The following variations were seen: C4084G, G6482A, C8066G, T8699C, C12897T, and C14442T. The changes in the amino acid that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, known SNP In variations include C4084G, G6482A, C8066G, T8699C, C12897T, and C14442T.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the nuclear hormone receptor of the present invention was determined to be located on a Bacteria Artificial Chromosome ("BAC"), Bac Accession AC018629, which is known to be on chromosome 17.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in nuclear hormone receptor protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a nuclear hormone receptor protein, such as by measuring a level of a nuclear hormone receptor-encoding nucleic acid in a sample of cells from a subject e.g., mRNA or genomic DNA, or determining if a nuclear hormone receptor gene has been mutated. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue.

Nucleic acid expression assays are useful for drug screening to identify compounds that modulate nuclear hormone receptor nucleic acid expression.

The invention thus provides a method for identifying a compound that can be used to treat a disorder associated with nucleic acid expression of the nuclear hormone receptor gene, particularly biological and pathological processes that are mediated by the nuclear hormone receptor in cells and tissues that express it. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. The method typically includes assaying the ability of the compound to modulate the expression of the nuclear hormone receptor nucleic acid and thus identifying a compound that can be used to treat a disorder characterized by undesired nuclear hormone receptor nucleic acid expression. The assays can be performed in cell-based and cell-free systems. Cell-based assays include cells naturally expressing the nuclear hormone receptor nucleic acid or recombinant cells genetically engineered to express specific nucleic acid sequences.

The assay for nuclear hormone receptor nucleic acid expression can involve direct assay of nucleic acid levels, such as mRNA levels, or on collateral compounds involved in the signal pathway. Further, the expression of genes that are up- or down-regulated in response to the nuclear hormone receptor protein signal pathway can also be assayed. In this embodiment the regulatory regions of these genes can be operably linked to a reporter gene such as luciferase.

Thus, modulators of nuclear hormone receptor gene expression can be identified in a method wherein a cell is contacted with a candidate compound and the expression of mRNA determined. The level of expression of nuclear hormone receptor mRNA in the presence of the candidate compound is compared to the level of expression of nuclear hormone receptor mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate nuclear hormone receptor nucleic acid expression in cells and tissues that express the nuclear hormone receptor. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue. Modulation includes both up-regulation (i.e. activation or agonization) or down-regulation (suppression or antagonization) or nucleic acid expression.

Alternatively, a modulator for nuclear hormone receptor nucleic acid expression can be a small molecule or drug identified using the screening assays described herein as long as the drug or small molecule inhibits the nuclear hormone receptor nucleic acid expression in the cells and tissues that express the protein. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen.

The nucleic acid molecules are also useful for monitoring the effectiveness of modulating compounds on the expression or activity of the nuclear hormone receptor gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in nuclear hormone receptor nucleic acid expression, and particularly in qualitative changes that lead to pathology. The nucleic acid molecules can be used to detect mutations in nuclear hormone receptor genes and gene expression products such as mRNA. The nucleic acid molecules can be used as hybridization probes to detect naturally occurring genetic mutations in the nuclear hormone receptor gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the nuclear hormone receptor gene associated with a dysfunction provides a diagnostic tool for an active disease or susceptibility to disease when the disease results from overexpression, underexpression, or altered expression of a nuclear hormone receptor protein.

Individuals carrying mutations in the nuclear hormone receptor gene can be detected at the nucleic acid level by a variety of techniques. FIG. 3 provides SNP information that has been found in a gene encoding the nuclear hormone proteins of the present invention. The following variations were seen: C4084G, G6482A, C8066G, T8699C, C12897T, and C14442T. The changes in the amino acid that these SNPs cause can readily be determined using the universal genetic code and the protein sequence provided in FIG. 2 as a base. As indicated by the data presented in FIG. 3, the nuclear hormone receptor of the present invention was determined to be located on a Bacteria Artificial Chromosome ("BAC"), Bac Accession AC018629, which is known to be on chromosome 17. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a nuclear hormone receptor gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant nuclear hormone receptor gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the nuclear hormone receptor gene in an individual in order to select an appropriate compound or dosage regimen for treatment. FIG. 3 provides SNP information that has been found in a gene encoding the nuclear hormone proteins of the present invention. The following variations were seen: C4084G, G6482A, C8066G, T8699C, C12897T, and C14442T. The changes in the amino acid that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control nuclear hormone receptor gene expression in cells, tissues, and organisms. A DNA antisense nucleic acid molecule is designed to be complementary to a region of the gene involved in transcription, preventing transcription and hence production of nuclear hormone receptor protein. An antisense RNA or DNA nucleic acid molecule would hybridize to the mRNA and thus block translation of mRNA into nuclear hormone receptor protein.

Alternatively, a class of antisense molecules can be used to inactivate mRNA in order to decrease expression of nuclear hormone receptor nucleic acid. Accordingly, these molecules can treat a disorder characterized by abnormal or undesired nuclear hormone receptor nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the nuclear hormone receptor protein, such as substrate binding.

The nucleic acid molecules also provide vectors for gene therapy in patients containing cells that are aberrant in nuclear hormone receptor gene expression. Thus, recombinant cells, which include the patient's cells that have been engineered ex vivo and returned to the patient, are introduced into an individual where the cells produce the desired nuclear hormone receptor protein to treat the individual.

The invention also encompasses kits for detecting the presence of a nuclear hormone receptor nucleic acid in a biological sample. Experimental data as provided in FIG. 1 indicates that nuclear hormone receptors of the present invention are expressed in humans in breast, brain, head-neck tissue, testis, placenta, retina, liver, kidney, HeLa cell tissue, and fetal liver-spleen. Specifically, a virtual northern blot shows expression in breast, testis, placenta, retina, head-neck tissue, and fetal liver-spleen. In addition, PCR-based tissue screening panels indicate expression in brain, placenta, liver, kidney, and HeLa cell tissue. For example, the kit can comprise reagents such as a labeled or labelable nucleic acid or agent capable of detecting nuclear hormone receptor nucleic acid in a biological sample; means for determining the amount of nuclear hormone receptor nucleic acid in the sample, and means for comparing the amount of nuclear hormone receptor nucleic acid in the sample with a standard. The compound or agent can be packaged in a suitable container. The kit can further comprise instructions for using the kit to detect nuclear hormone receptor protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the nuclear hormone receptor proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the nuclear hormone receptor gene of the present invention. FIG. 3 provides SNP information that has been found in a gene encoding the nuclear hormone proteins of the present invention. The following variations were seen: C4084G, G6482A, C8066G, T8699C, C12897T, and C14442T. The changes in the amino acid that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified nuclear hormone receptor gene of the present invention can be routinely identified using the sequence information disclosed herein can be readily incorporated into one of the established kit formats which are well known in the art, particularly expression arrays.

Vectors/host Sells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from $E.$ $coli$, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, $E.$ $coli$, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteronuclear hormone receptor. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion $E.$ $coli$ expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example $E.$ $coli$. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as nuclear hormone receptors, appropriate secretion signals are incorporated into the vector. The signal sequence can be endogenous to the peptides or heterologous to these peptides.

Where the peptide is not secreted into the medium, which is typically the case with nuclear hormone receptors, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a nuclear hormone receptor protein or peptide that can be further purified to produce desired amounts of nuclear hormone receptor protein or fragments. Thus, host cells containing expression vectors are useful for peptide production.

Host cells are also useful for conducting cell-based assays involving the nuclear hormone receptor protein or nuclear hormone receptor protein fragments, such as those described above as well as other formats known in the art. Thus, a recombinant host cell expressing a native nuclear hormone receptor protein is useful for assaying compounds that stimulate or inhibit nuclear hormone receptor protein function.

Host cells are also useful for identifying nuclear hormone receptor protein mutants in which these functions are affected. If the mutants naturally occur and give rise to a pathology, host cells containing the mutations are useful to assay compounds that have a desired effect on the mutant nuclear hormone receptor protein (for example, stimulating or inhibiting function) which may not be indicated by their effect on the native nuclear hormone receptor protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a nuclear hormone receptor protein and identifying and evaluating modulators of nuclear hormone receptor protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the nuclear hormone receptor protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the nuclear hormone receptor protein to particular cells.

Methods for generating trasgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, nuclear hormone receptor protein activation, and signal transduction, may not be evident from in vitro cell-free or cell-based assays. Accordingly, it is useful to provide non-human transgenic animals to assay in vivo nuclear hormone receptor protein function, including substrate interaction, the effect of specific mutant nuclear hormone receptor proteins on nuclear hormone receptor protein function and substrate interaction, and the effect of chimeric nuclear hormone receptor proteins. It is also possible to assess the effect of null mutations, that is mutations that substantially or completely eliminate one or more nuclear hormone receptor protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule consisting of a nucleotide sequence selected from the group consisting of:
   (a) a nucleotide sequence that encodes a polypeptide having an amino acid sequence comprising SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A vector comprising the nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide.

5. An isolated polynucleotide consisting of the nucleotide sequence of SEQ ID NO:1.

6. An isolated polynucleotide consisting of the nucleotide sequence of SEQ ID NO:3.

7. The vector of claim 2, wherein said vector is selected from the group consisting of a plasmid, a virus, and a bacteriophage.

8. The vector of claim 2, wherein said isolated nucleic acid molecule is inserted into said vector in proper orientation and correct reading frame such that a polypeptide comprising SEQ ID NO:2 may be expressed by a cell transformed with said vector.

9. The vector of claim 8, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2086
<212> TYPE: DNA
<213> ORGANISM: Homo sapiens

<400> SEQUENCE: 1

| | | | | | |
|---|---|---|---|---|---|
| aacagcacga | gggcgagggg | acgtctcctc | tcccccagct | gctctgctcg | gatggcgccg | 60 |
| ccggctgagt | gacgggggcg | gcgcgcagga | cttcccagct | cggacctctt | gccttcgagg | 120 |
| ggaaagatgt | acgagagtgt | agaagtgggg | ggtcccaccc | ctaatccctt | cctagtggtg | 180 |
| gatttttata | accagaaccg | ggcctgtttg | ctcccagaga | agggctccc | cgccccgggt | 240 |
| ccgtactcca | ccccgctccg | gactccgctt | tggaatggct | caaaccactc | cattgagacc | 300 |
| cagagcagca | gttctgaaga | gatagtgccc | agccctccct | cgccaccccc | tctacccgc | 360 |

-continued

```
atctacaagc cttgctttgt ctgtcaggac aagtcctcag gctaccacta tggggtcagc      420
gcctgtgagg gctgcaaggg cttcttccgc cgcagcatcc agaagaacat ggtgtacacg      480
tgtcaccggg acaagaactg catcatcaac aaggtgaccc ggaacccctg ccagtactgc      540
cgactgcaga agtgctttga agtgggcatg tccaaggagt ctgtgagaaa cgaccgaaac      600
aagaagaaga aggaggtgcc caagcccgag tgctctgaga gctacacgct gacgccggag      660
gtgggggagc tcattgagaa ggtgcgcaaa gcgcaccagg aaaccttccc tgccctctgc      720
cagctgggca aatacactac gaacaacagc tcagaacaac gtgtctctct ggacattgac      780
ctctgggaca agttcagtga actctccacc aagtgcatca ttaagactgt ggagttcgcc      840
aagcagctgc ccggcttcac caccctcacc atcgccgacc agatcaccct cctcaaggct      900
gcctgcctgg acatcctgat cctgcggatc tgcacgcgt acacgcccga gcaggacacc       960
atgaccttct cggacgggct gaccctgaac cggacccaga tgcacaacgc tggcttcggc     1020
cccctcaccg acctggtctt tgccttcgcc aaccagctgc tgcccctgga gatggatgat     1080
gcggagacgg ggctgctcag cgccatctgc ctcatctgcg agaccgcca ggacctggag       1140
cagccggacc gggtggacat gctgcaggag ccgctgctgg aggcgctaaa ggtctacgtg     1200
cggaagcgga ggcccagccg cccccacatg ttccccaaga tgctaatgaa gattactgac     1260
ctgcgaagca tcagcgccaa gggggctgag cgggtgatca cgctgaagat ggagatcccg     1320
ggctccatgc cgcctctcat ccaggaaatg ttggagaact cagagggcct ggacactctg     1380
agcggacagc cggggggtgg ggggcgggac ggggtggcc tgcccccccc gccaggcagc      1440
tgtagcccca gcctcagccc cagctccaac agaagcagcc cggccaccca ctccccgtga     1500
ccgcccacgc cacatggaca cagccctcgc cctccgcccc ggcttttctc tgcctttcta     1560
ccgaccatgt gaccccgcac cagccctgcc cccacctgcc ctcccgggca gtactgggga     1620
ccttccctgg gggacgggga gggaggaggc agcgactcct tggacagagg cctgggccct     1680
cagtggactg cctgctccca cagcctgggc tgacgtcaga ggccgaggcc aggaactgag     1740
tgaggcccct ggtcctgggt tcaggatgg gtcctggggg cctcgtgttc atcaagacac       1800
ccctctgccc agctcaccac atcttcatca ccagcaaacg ccaggacttg ctcccccat      1860
cctcagaact cacaagccat tgctccccag ctggggaacc tcaacctccc ccctgcctcg     1920
gttggtgaca gaggggggtgg gacagggcg ggggttccc cctgtacata ccctgccata        1980
ccaaccccag gtattaattc tcgctggttt tgttttttatt ttaatttttt tgttttgatt    2040
tttttaataa gaatttttcat tttaagcaca aaaaaaaaaa aaaaaa                   2086
```

<210> SEQ ID NO 2
<211> LENGTH: 457
<212> TYPE: PRT
<213> ORGANISM: Homo sapiens

<400> SEQUENCE: 2

```
Met Tyr Glu Ser Val Glu Val Gly Gly Pro Thr Pro Asn Pro Phe Leu
 1               5                  10                  15

Val Val Asp Phe Tyr Asn Gln Asn Arg Ala Cys Leu Leu Pro Glu Lys
            20                  25                  30

Gly Leu Pro Ala Pro Gly Pro Tyr Ser Thr Pro Leu Arg Thr Pro Leu
        35                  40                  45

Trp Asn Gly Ser Asn His Ser Ile Glu Thr Gln Ser Ser Ser Ser Glu
    50                  55                  60

Glu Ile Val Pro Ser Pro Pro Ser Pro Pro Pro Leu Pro Arg Ile Tyr
```

-continued

```
                65                  70                  75                  80
Lys Pro Cys Phe Val Cys Gln Asp Lys Ser Ser Gly Tyr His Tyr Gly
                        85                  90                  95
Val Ser Ala Cys Glu Gly Cys Lys Gly Phe Phe Arg Arg Ser Ile Gln
                100                 105                 110
Lys Asn Met Val Tyr Thr Cys His Arg Asp Lys Asn Cys Ile Ile Asn
                115                 120                 125
Lys Val Thr Arg Asn Pro Cys Gln Tyr Cys Arg Leu Gln Lys Cys Phe
            130                 135                 140
Glu Val Gly Met Ser Lys Glu Ser Val Arg Asn Asp Arg Asn Lys Lys
145                 150                 155                 160
Lys Lys Glu Val Pro Lys Pro Glu Cys Ser Glu Ser Tyr Thr Leu Thr
                165                 170                 175
Pro Glu Val Gly Glu Leu Ile Glu Lys Val Arg Lys Ala His Gln Glu
                180                 185                 190
Thr Phe Pro Ala Leu Cys Gln Leu Gly Lys Tyr Thr Thr Asn Asn Ser
                195                 200                 205
Ser Glu Gln Arg Val Ser Leu Asp Ile Asp Leu Trp Asp Lys Phe Ser
            210                 215                 220
Glu Leu Ser Thr Lys Cys Ile Ile Lys Thr Val Glu Phe Ala Lys Gln
225                 230                 235                 240
Leu Pro Gly Phe Thr Thr Leu Thr Ile Ala Asp Gln Ile Thr Leu Leu
                245                 250                 255
Lys Ala Ala Cys Leu Asp Ile Leu Ile Leu Arg Ile Cys Thr Arg Tyr
                260                 265                 270
Thr Pro Glu Gln Asp Thr Met Thr Phe Ser Asp Gly Leu Thr Leu Asn
                275                 280                 285
Arg Thr Gln Met His Asn Ala Gly Phe Gly Pro Leu Thr Asp Leu Val
            290                 295                 300
Phe Ala Phe Ala Asn Gln Leu Leu Pro Leu Glu Met Asp Asp Ala Glu
305                 310                 315                 320
Thr Gly Leu Leu Ser Ala Ile Cys Leu Ile Cys Gly Asp Arg Gln Asp
                325                 330                 335
Leu Glu Gln Pro Asp Arg Val Asp Met Leu Gln Glu Pro Leu Leu Glu
                340                 345                 350
Ala Leu Lys Val Tyr Val Arg Lys Arg Arg Pro Ser Arg Pro His Met
                355                 360                 365
Phe Pro Lys Met Leu Met Lys Ile Thr Asp Leu Arg Ser Ile Ser Ala
            370                 375                 380
Lys Gly Ala Glu Arg Val Ile Thr Leu Lys Met Glu Ile Pro Gly Ser
385                 390                 395                 400
Met Pro Pro Leu Ile Gln Glu Met Leu Glu Asn Ser Glu Gly Leu Asp
                405                 410                 415
Thr Leu Ser Gly Gln Pro Gly Gly Gly Arg Asp Gly Gly Gly Leu
            420                 425                 430
Pro Pro Pro Gly Ser Cys Ser Pro Ser Leu Ser Pro Ser Ser Asn
                435                 440                 445
Arg Ser Ser Pro Ala Thr His Ser Pro
    450                 455

<210> SEQ ID NO 3
<211> LENGTH: 17000
<212> TYPE: DNA
<213> ORGANISM: Homo sapiens
```

```
<220> FEATURE:
<221> NAME/KEY: misc_feature
<222> LOCATION: (1)...(17000)
<223> OTHER INFORMATION: n = A,T,C or G

<400> SEQUENCE: 3
gtccttgggt agcatgtaca tttccatccc ttccttttat atatgggggt aataggatac      60
cccctcctcc aggggtatcc cctctttcta gggacctacc caagctaggc ctttcttcca     120
gtgaaacgtg catcccgagg gcttctagga tgaagtagtc cactggaagg caccagctct     180
tcctttatc tctccagagc tggacagtgc caggggggcc ggtactggtt ccccagctag      240
gagacacctt gggcggggct tgctcgccg aagcacgca gagcgtgggg aggagggccc       300
cctctgcctg tgtttgtgcc aacagcaccc gcgctgccgc gtcgggttcc ggcggccgga     360
gtcacacatg atgtcacaga caatgacaca agccggtgtc tcattccgac acagcgtccg     420
agctgcacaa tgtcacaccc gggtgccaaa cacttggccc cgcgcgaccc ggccctacgc     480
ctcctgccgc cgctctccgc gtctccgggg gaggtggccc ggttcggccg gcagggggc      540
tggcgggcga gccccgcggg cgggctggcg agcgggtgat gtcacgggca gcggtgggtg     600
ggtcactcgg aggtgaggcg ccgccaggcg agttcagcga gagttcagcc gcattgcatt     660
aggcaaatga ggcccggcct gggtgggggt gtgtgttaag gggaggacac cgggaccacc     720
cccctcttcc ccgcccacc acctcctcca ccacggcttc gctcggccag ggactgacca      780
aaccttgggg gagcctggga gccggaactg gtacaagggg aggacgcccg ccctcttcc      840
gtccttgtcc cctcgcagcc ccctcctctc cctgtactcg gcgtccctct gtactctgtg     900
tactcctcat ctggagcctt tccccttcc tgcttctctc ctctcctccc ccttcccagg      960
ctgccccac ttgcctgtcc acatgccgcc tctccctctc ggttccctgc gtttctcccg     1020
ctgcagccgg acgcgccggg aatgggttaa gccaggggcg gtgcctggac ggggcggggc    1080
ggtggaaagg gggtggtgcc cggaggggag ggggcgcgca gagctggggt ggggggggccg   1140
tggcgcgtac caccagagac cgagcgagtc gccagctgcc cctggcctgg cggggcgga    1200
accgcgcggg atccccaccc ccacccggaa tcctcgccac ggagaatccc tggagaagcc    1260
ccggatcccc ggctgggagg aggaagtgct cgttgacccc cagccccgcg ctgatcccgc    1320
ccccggcctg cggacttggg gagccgctgt actctgcctc ggacgccacg agactctaga    1380
cgggagtccc ctcgaggtga agccgctgag ttcccgggcc ccgccaggct tccctgggag    1440
agccgacgga cccccctcc cagcacacac aacttcctg cttttcaccg ggactggcgg     1500
agcggccggc ggacttagac gcggggactt cagggcaggg ggcgccccct gcccgggtca    1560
ccagtcgggg cgaggggacg tctcctctcc cccagctgct ctgctcggat ggcgccgccg    1620
gctgagtgac gggggcggcg cgcaggactt cccagctcgg acctcttgcc ttcgagggga    1680
aagatgtacg agagtgtaga agtgggggt cccacccta atcccttcct agtggtggat      1740
ttttataacc agaaccgggc ctgtttgctc ccagagaagg ggctccccgc cccgggtccg    1800
tactccaccc cgctccggac tccgctttgg aatggctcaa accactgtac gtaccggcct    1860
ctcagtctgc tgttgtaggg ggtgggagtg ggcggtaggg cttccactac tactcggggg    1920
tgagagtccc ggggtgtagt ggaggtcctg tctctacctt tcacttaacc cgtgttgccc    1980
ttgctggaca attgaaccct cccggccgca ccctccccc agtaacccta agtgcaattt     2040
gtgttagatt agggctgagg aactttgaga gttccttctt ttcaagcaac attcctttca    2100
tctctttgtt tcacttcttc ccaggagaaa tgaagcccaa gccccctttg gccccagtt     2160
```

```
tgtatattct ttcttggcct tgggaaatcc caaaaaggtt tcaccagcaa ggcttgggaa    2220
ggggtggggg ggtaaaaggg ttccctggtc ttgtggtggg ttttggtct tgcttacccg    2280 gggggggnnnn nnnnnnnnnn nnnnnnnnnn nnnnnnnnnn nnnnnnnnnn nnnnnngaag  2340
ggctctgtgc acactcagga gctcggagca ccagggtgta cacctgggca ttttcctgcg    2400
cagctgtgag gcagtgtaca ctgggtgggc gggagcaggc gcaaggggt tattgttaga    2460 tggctcaggt ttcttcccct cctgggcttt ggctctttg ctggaggga agctcttccg     2520 tggaggatct cccaccttcc tggacctgct gcctccctcc tgcctgccag ggaggagggg    2580
tggagtgggt ctcgggggggg ccctggcaga ttggaaaagg ttgaagggca aaggacttac   2640
cccacccctc ttgctgggag aagagagacc tgagatggac agacagccca cctctgccct   2700
cccagagcca cttctatccc agcttttcct attgtcctgc ccccgaccat ttcctctagg   2760
gccgaatctg ctgtgtggct gtagacacaa gagggaaggt atcacccttg actttggaag   2820
aagagagagt gagaggatga ctctaggacc ctttttctca ttctcccagt gctggagcaa   2880 gaccccctc ccctagggg atagttggag cagggctgcc cagagtcacc ccttccactg     2940
ccttggccac cttctccaga gggctggaga gaagctggga tctgagacct tggtctccag   3000
cccctgtctc ttcttagccc atggggacag ctcagctctt cctggcccag aactggagag   3060
ggaggaggat cacagagagt aggacaggca gtgtattggt gagcccttcc cctaaaccac   3120
tggacatggg gaagtggaga cctgtcccca catccattct ggggtggggt agtagaccta   3180
gaggcctggg tttccagttc ccgtagtctg agcgtgggtg tgcatatata agtgagtgag   3240
gtgtcagtgg actcgggtcc tgaggctgtg aggttgggag tgatgggggt ctgggggctt   3300
gccttgaggc acaggaagga cccggagtct gagggtggca actagactca gtctagaata   3360 tgtgggcca atgccaccac cttggaaggg tccccttggg tgtgttggaa gtccgctggt    3420
gactggagct gcctccagcc ccctcttggg gaattctcca ctctcccctt tactgccact   3480
gaaggtggga agagcaggtt ggctctggga ggaggtggcc tgggttctgc agggccctag   3540
ggacattgcc tccctcccca gagccctcat ttcggtgcat tagaggacaa gggggggtgc   3600
acaggatgtg gctccccatc tgtctcccac caatctccgc cactcacacc tccgcccgct   3660
cccagacgtc caagaatgtg aagcacgtgg atgcccgtag ttgggggagg gggagacgct   3720
tatcaggcgg ccgctgggct aggggccttc ttccgctgcc gcggtacacc cagagctacc   3780
cccgcctctc cccgggagga ggaaggacgc tacagagggc cctacgcccc ctccccaacc   3840
atccccaggg gctgcgaggg gagctgcgga ggagcgggcg ccagctggat tgggagggga   3900
gccgctggcc ggggggcccgg ctgatttcct gctgatctcc tccaggaaac cggcccttg   3960 tgcgagcctg cgaacggctc gggggcgtgg ggaatccgga gtggagcgct ctgcgccgcc   4020
cgccctgcca ggatgggggag cgagggaggg gcaccctggc agcgtcggcg ggagggacg   4080 cctggcttcc tgggtcagtt ccagtcctct gttgggcgct ggaactttga gctgagaagg   4140
tgtggtcctt ctctagcccg agtccttctg caggaagagg agagattggt gggctgggcc   4200 tctgggagg gaggttagca gggatgggcc aggcccgggc agtccctccc ccgttggtgt   4260
ccctccccac tccacctgtg tgtgcaggga gttatggccg tgtcctaact cttgcagagg   4320
ctgtgaggat tccggagttc cccacacctc cggccttggt ccttgtacct cacctccttg   4380
gactgctggc tggaggcctg gggaggtggg gcatcgagct ctgggttcaa agggcagagc   4440
agggaaacct cagagctggg ttacctgggt gacaggtggg gatgtgctgg aggtaggggg   4500
caggctatgt tacagcctcc aaggcagtca agctgccgtt gggtgggcta aaaggaggcc   4560
```

-continued

```
ttgcccagcc taaactgtag tccttgcctc tggtcatctc tcccattctg ccaaaaaata    4620
attttaaaaa gcacattctc tcagttccgt aaacaccctc tgttggactt tgctttagct    4680
ccatgttttt atggcttttt gccctctagt ctgtcccagg ccttagagct gtttacctct    4740
catcctggta tcccccatga ctccccatac cctagctccc ctcgtgacat cccgctctgt    4800 accccccaaag ctccctcagt cctttctccc tctccagtct ggttcatttt agaagtgggg    4860
```

-continued

| | |
|---|---|
| tgtcaggaca agtcctcagg ctaccactat ggggtcagcg cctgtgaggg ctgcaaggtg | 6960 |
| agttgaaggg gtcattggga aggacagctt gatgaggtca atggggatgt ccccacttct | 7020 |
| gtgtcctggg agtgtgcagt tgggggggtgt ccctgaattg ctgctcttct ttctctgtgg | 7080 |
| aagttggcag caagcagggg acacctacca cagtttcccc acaggtcctc cccataaat | 7140 |
| gtgcagggct ccctcaaacc agaggtcccc tcctgcctca gctcctttcc ctgtctctat | 7200 |
| cctccagctg gcagggcgta cgcctgctct gccaccgctg cccaggttgc catggtgagc | 7260 |
| tggctgccga ctggctcttg gctggggacc caggaggcct ccccggcgg ccctgcctga | 7320 |
| acctcaccat ggcagcctgg caggaggcag ttaggagcag gcaccctgcc ttagcttccc | 7380 |
| cttcaggtgc ccgggctgtg ggctccccag tgtctggctg gatttcccca tcctcacgtt | 7440 |
| aggtgccagg gtgcaggtat acctggtcct tagcagccct gcgcccggct tctcctcctt | 7500 |
| tccctggggc ctgagcctct gtgtgcgttt cttcctccag agattggggc tcagaatctt | 7560 |
| cacagctttg ggccttgcag ctctgggctg ctcttcagcc tggagtagct atccccagat | 7620 |
| gtgggacgga ggtcaagggc aaagcacaag gactcaggct gtgtgtctgc ctgtcctgtc | 7680 |
| tggttgttcc tggtctgttc ttcctctgtc cgcctgtccc tctggtcagc ctgtatgtgg | 7740 |
| agcccctggc cagcctgggt ctgtgtctgt gatgggtcgg tgcacacctg tcttggtgaa | 7800 |
| ctcacatctt tctgccttgc tcctgagtgc atgtgtgtgt tcgcctccat ttctctggcc | 7860 |
| agcccgtgta tctgcctcct ggcctcttcg ggcttgtctt cttttcctgt gttctgagtt | 7920 |
| cagggggtgtg ggttccagat ccctggctgt tgcccagtta gccccatgtc ttcctatttc | 7980 |
| tgactcacca gcagccctga ggtctttttcc ctggaaggga ggagtcaggt gtgtgctgtg | 8040 |
| ggttgggggga agactcctgc ccatcctgca gtgttgaggc aggtactggg attctcctga | 8100 |
| ggaggatcct tttaggtgaa tcattctccc cagcttttct ggcctgctca ggtaggcgat | 8160 |
| gggcaaacgc ttgggggcag cagctggcct ggccctcctc ccctagactg agaccgtagc | 8220 |
| caggcactgc tcccactgtg ggtgtggaca acctgactcc ctcccctcca tacccagggc | 8280 |
| ttcttccgcc gcagcatcca gaagaacatg gtgtacacgt gtcaccggga caagaactgc | 8340 |
| atcatcaaca aggtgacccg gaaccgctgc cagtactgcc gactgcagaa gtgctttgaa | 8400 |
| gtgggcatgt ccaaggagtg tgagtgccat agggcagggg ccgagtcccg cctcagttgg | 8460 |
| ggtctcagat gctcctaaag accaagggag cagggctctg tggatgtttg tgcacatgca | 8520 |
| tgaacacgca tgccgtggtg tgcgggctca cggttgagga tggtttgtgt gtagctgcaa | 8580 |
| ggacctgttt gcgagtctgg ctggctgtgt gtccacgggc aggtctgtgc tccgggaccg | 8640 |
| tgtatgtgta accattcctg tttctgcacg tctggctgtg tgtgcttgcg tatgtgtgtg | 8700 |
| tgtgtgcatg ctccaggatg gctttcttcc aggccgtgct tggttttggg gtggggctca | 8760 |
| gaggcatagg cagtcccttc tgattgtgag tcttagggga ggggcttgaa ttctgagggg | 8820 |
| tgcttggctg gacttatgtg tgtatggggg ggtggaaggg ctggcacaag gatccaaaag | 8880 |
| ccattgtcta gttaagcctg ggattcagag ttggaagaaa gaattgggac ttctcagatc | 8940 |
| ccagaggaaa cggggtttcc actttgggct cagctgaggc ctgatggagg gagggaggga | 9000 |
| aaggctggac aggagaccc tcttgtgttg aatcatgggt gttgccatgg tgaccggtga | 9060 |
| ttgatgatgt cagagataaa tgacgctgac agacgcctcc ttgtctgcgt ggccgttgcc | 9120 |
| atggagcctg agccttgggg gatgggatgg gggaggggc tgcaggaccc cctagccctt | 9180 |
| tgtggggagg gcagtgggga gggggcacgg gtgagatggt tctgactgtt gcacgaagag | 9240 |
| ccccagacag gaatggaggg gactggagtg tcctgccaca ggaggctggg ggtgccttgt | 9300 |

```
cctgagccca ggaagtggtg gctcctgctg caagagtggg tgacaactca agacccacaa   9360
gcctggaacc cttcgcttaa gggctgtcac ctcctcctct ctgtttgtgc caccttctgc   9420
tcttttcatg gcagaaggac cagggagggg acccttctc cctcccaccg ccaactcccc    9480
ttctccctcc caccgccaac tcccctctc ccggctgctc tgtgcccgg agctgagcag     9540 ctgccatttc aatagaatta aagcttccga atgataaacg tcttgtcaca gctgcaattt   9600
tctcttccca aattatcccc ccactctccc tctccctctc ccttctctcc cctgcacttt   9660
attgaatttg cagaatcgac atgagtgatc tccaaattat gccagctacc cccacctcgc   9720
taccccctcc ctgagcccct cccccacccct cccttcctcc cgcgtcagca gccaccacca  9780
ccagccctgt gagtgattgt gtgtctggat aatcggctgg taacgacccc atcgcttctt   9840
taaagccgag tggtgtgtgc ggctcagcgc ccctggtgat ttgtcagctc cccagctaat   9900
gggccaagag attctccccg ccaggtcccc cactctcagg ctggggagcc ctactcccca   9960
cttgccccag gagctgctca gagccagtcc caagggaccc ccaggagac tgcagctggg   10020 agggctgggt gagtggaggc gggagaagga ccttcctggg gaaagaggag gcagagcacc   10080
taggagggca ccgtcgcctg gagtgtgagc tggagtagac gcgtggggga tagcatgcgg   10140
ctggctatgg ggtggggtgg ggggtgtgtg cagggccaca gctgtgctca tggggcttct   10200
ggggcagaac ttgatgtgtg ggttgggtgg gcatggaggg ctggagtgcg tggcaatgcc   10260
ttgcctgccc gtgaacgcgt gctgtgtgcg cgtgcttaca agcctgggtg acctcctcag   10320
cagctggcag ctctctgtca ggctgggggt ggacgaggcc ctgagcagcc tgcagctgcc   10380
ctcttaaccc cctctgccct ccacagctgt gagaaacgac cgaaacaaga agaagaagga   10440
ggtgcccaag cccgagtgct ctgagagcta cacgctgacg ccggaggtgg gggagctcat   10500
tgagaaggtg cgcaaagcgc accaggaaac cttccctgcc ctctgccagc tgggcaaata   10560
cactacggta tggcttttccc ccggcctgca gggtgggatt tgcccagggc cacagggcca   10620
ggatgggccc ctctcaggca ccccttcttg tgccaggcaa gatctctgcg tccttcccct   10680 ccctctctt ctccctcctc ctgctgcctc ttcccaagga gctcccagga agtgaaggct    10740
gggtagaggg caggcctgtg ggggctggag ccaggctgag aagggtgcc atggagaaga    10800 aggccctcac tctccctcct cccccagaac aacagctcag aacaacgtgt ctctctggac   10860
attgacctct gggacaagtt cagtgaactc tccaccaagt gcatcattaa gactgtggag   10920
ttcgccaagc agctgcccgg cttcaccacc ctcaccatcg ccgaccagat cacccctcctc   10980 aaggctgcct gcctggacat cctggtgagg gtctgcaccc tggcccccag gcactgcccc   11040
tgtgtcctgg gtagatgtcc ttccagccag acagccaccc tcctaaatgt ctgtctgcaa   11100
tcaacctgtc caaatgccca ccgcccaaat gtctgccctt cctctcccca tatgtccacc   11160
tgtccactcg tctccctgtc cactcagcca cctagcagcc agatgtgcag gagctcacct   11220
gttcacccat acacatatcc agccacccag ccatccatcc atttagccag taataaagat   11280
tcacgtagga gccaggtgca gtggctcata cctgtaatcc cagcactttg ggaggccgag   11340
cgaggcagga ggatcacttg aggctggaag ttcaagacca ccctgggcaa catagtgaga   11400
ccttatttct gcaaaaaact aaaaagattc acctaggatc ctctggccag tgttcgagct   11460
gggtgtcagg aacccagcgg tgaatgcacc accatcccct ctcttgaaaa ccttccatgt   11520
gaggcaagag ataagtcaac agaggttgca aaactgtgat caatgcttcc tggagattgg   11580
gggagggctt gtgactgctt gggcctgaag gatgatgtct cagaggaggt gacatctagg   11640
```

```
ggtttgtaga gggggaggtg agagggtagc cctaactcag gagcaggaag tgaaagactt    11700
gctgctgtga ggccatgctg agctcagggg actgccgggc actcggtgag gtgagcccga    11760
gggtagactg ggctggaggc tggatgcagg gggtgggggc aggaagaggt ggtgggaact    11820
gccaaagcct aggctggagg gagcactctc cttcctgctg tccctgacaa gggctcggtc    11880
cacctgttcc ctcttggtca cctccagggt ggggaacctg ggatttgacg agactgtcat    11940
ttctttttat gtttttcttt tttgagatgg agtttcactc ttgtcaccca ggctggagtg    12000
cagtagtatg atcttggctc actgcagcct gcaactgctg cctcccgggt tcaagcgatt    12060
ctcctgcctc agcctcctga gtagctggga ttacaggcac cgccaccac  acccggctaa    12120 tttttgtatt tttgtagaga cggggtttca ccatgttggc caggccggtc tcgaactcct    12180
gacctcaggt gatcctcccg cgtgagccgg cagactgtca tttctccatg ggcacctctg    12240
aatgttgagg cgggtgatgg gtgggaggtt tagattgtgc tgcctgcagg ggctcccatc    12300
cccatgccgt ggatgcagga ggtgccgtct ggttcctgc  aaccacattc aagccaatac    12360
acatttactg agcgcttgtt gtgtacctca tcctgggagc tgtaggcagc agcccagtgt    12420
tccttagctc ctagaaattc taggtcccct ctacattctt tgcatgtagg caggatgacc    12480
tggacctgca ctatccagta cagtagctgc tcaccacatg tgactcttta aatttaaatt    12540
aattaaaatt aaactcaatt cagttcctca gttgcattag ccacatttca agtactcagt    12600
agacgcatgt ggctggtggc tgaggtatgg atggtgcaga cgtagaacct ttccatcatt    12660
gtagaaaatt ctatcagaca gcattgctcc ggccacctgc caggtggtcc tccgggagtg    12720
ctggtgcgga gtgctggtgc cgagtgctca gagtgggttc gggttcagtc cctgaaccca    12780
agcatcctct gcacccagat cctgcggatc tgcacgcgt  acacgcccga gcaggacacc    12840
atgaccttct cggacgggct gaccctgaac cggacccaga tgcacaacgc tggcttcggc    12900
cccctcaccg acctggtctt tgccttcgcc aaccagctgc tgcccctgga gatggatgat    12960
gcggagacgg ggctgctcag cgccatctgc ctcatctgcg gaggtgggca ggggcctgg    13020 gtctgggggc tgggctggga cggggtgca gccctggagt ctcttccagg gagctctttc    13080
aggccacctc tgttaggtat ctctagaggg cagggtctgg tctgcaacta cacagcaagg    13140
gggccatgtg gggcctggac tcctgttccc gatttctggg caacacccct tctagggagg    13200
ttaagagtga gggtttgagg gtcggaccaa ccagggtcac ctcctggccg atgcatgacc    13260
ctgagcaggt tgctgaactt ctctgggcct ccgtttctgt acagtggggg cggtaacggt    13320
ctctagctca tgaagttgat gggaggatta cggtggtaac agatactgtg caggtgccca    13380
gagcgagctc cagtgcttgt tagttgctat tttattgttg tgatttctgc catttcatct    13440
ggtttccaga ataacagggg ggagtgggag cctgcctggg aaccctctcc ctgcttgagg    13500
atggcactgc ccatttgggg tcccatccca ctaactgggc tcagggaggg tttggggcac    13560
cccctcaccc tcagctcccg ttgctccctt ttaagggcct ctgtaccctg cggcagcaga    13620
gaccccatgc cctgccctgt gtggggaggc gcctgcgagc tgccctcctc catggcctgg    13680
gcaggcacgc ccccggtgg  ccgaggctgg gggtgcagct tgttcccag  ctgctcaggg    13740 ggtggttctg cttcctcaga ccgccaggac ctggagcagc cggaccgggt ggacatgctg    13800
caggagccgt gctggaggc gctaaaggtc tacgtgcgga agcggaggcc cagccgcccc    13860
cacatgttcc ccaagatgct aatgaagatt actgacctgc gaagcatcag cgccaagggt    13920
gaggctcaca gacctggagg ggtaccggcc cccgacacct ggcccaggcc cccacatcca    13980
agccagcacc ccatgtcttt gtgccaggac aatacgacac ctgtccccat ctgtgtctag    14040
```

-continued

```
gctgaggtcc cctagtgact ccactttgcc gaggtggccc gcctgtgtca cctttgtgtg   14100
gtagttcaga tcgtggctct ggaaccagac acgtgggtgt gtgtccttgt gtgggtcact   14160
caacagctcc tagctacagt ttcccttccg agggcgggga taacattcgt gtttacagag   14220
gggtcgggat gatccctagc acacagcaca ggggaaggaa gggcttggcg tctagcccag   14280
gccggcagtc tggccctgga gccggagttc gggaccactt tgccccattg ccaccagcct   14340
ctggacctgg gggcttaaga gagctggctc gtgtcaaaga actgaatccc aagaaagatg   14400
ctaatatcag cagtattgat cttcccacct cgagccaggc ttgctgggc tggggtggg   14460 agggctggcc cagcgtgctg acctctgccc cctcctttcc tgcagggct gagcgggtga   14520 tcacgctgaa gatggagatc ccgggctcca tgccgcctct catccaggaa atgttggaga   14580
actcagaggg cctggacact ctgagcggac agccgggggg tggggggcg gacggtggt   14640 ggccttctgc agtaaaaagt gccctgatgc caccattgcc gtaaaacta atgcccaatt   14700 gtgataagga gctaccgggg tacacacggg gactggttca aatgggcat cgccgaagca   14760 tgtgatgcta tgaacttaat cggactatta ttctggtgga tcctcaaacc agcatcgcaa   14820
cctggacact cttttgcatg gtcgttatta tctccggtag actccttgcc tccctttac   14880 ataaaaaggc ctcccccgac aaaagggtc agttcgatcc ccactttcgg ttcgggagcc   14940
taccgtgtgc caaaggccct taatctcgaa aatatcccaa ttacctgatg tcgtgcgacg   15000
cctaaaaatt ccccgtgttg ccaccactgc ttgaaacccc caagcttggg tgttaatccc   15060
gaattggggg ccccccgtnn nnnnnnnnnn nnnnnnnnnn nnnnnnnnnn nnnnnnnnnn   15120
nnnnnnnngg gccccccgc caggcagctg tagccccagc ctcagcccca gctccaacag   15180
aagcagcccg gccacccact ccccgtgacc gcccacgcca catggacaca gccctcgccc   15240
tccgccccgg cttttctctg cctttctacc gaccatgtga ccccgcacca gccctgcccc   15300
cacctgccct cccgggcagt actggggacc ttccctgggg gacggggagg gaggaggcag   15360
cgactccttg gacagaggcc tgggccctca gtggactgcc tgctcccaca gcctgggctg   15420
acgtcagagg ccgaggccag gaactgagtg aggcccctgg tcctgggtct caggatgggt   15480
cctgggggcc tcgtgttcat caagacaccc ctctgcccag ctcaccacat cttcatcacc   15540
agcaaacgcc aggacttggc tcccccatcc tcagaactca caagccattg ctccccagct   15600
ggggaacctc aacctccccc ctgcctcggt tggtgacaga ggggtggga caggcgggg   15660 gggtccccc tgtacatacc ctgccatacc aaccccaggt attaattctc gctggttttg   15720 ttttattt aattttttg ttttgatttt tttaataaga attttcattt taagcacatt   15780
tatactgaag gaatttgtgc tgtgtattgg ggggagctgg atccagagct ggaggggtg   15840 ggtccggggg agggagtggc tcggaagggg ccccccactct cctttcatgt ccctgtgccc   15900
cccagttctc ctcctcagcc ttttcctcct cagttttctc tttaaaactg tgaagtacta   15960
actttccaag gcctgccttc cctccctcc cactggagaa gccgccagcc cctttctccc   16020
tctgcctgac cactgggtgt ggacggtgtg gggcagccct gaaaggacag gctcctggcc   16080
ttggcacttg cctgcaccca ccatgaggca tgagcaggg cagagcaagg gccccgggac   16140
agagttttcc cagacctggc tcctcggcag agctgcctcc cgtcagggcc cacatcatct   16200
aggctcccca gcccccactg tgaaggggct ggccagggc ccgagctgcc cccacccccg   16260
gcctcagcca ccagcacccc catagggccc cagacacca cacacatgcg cgtgcgcaca   16320
cacacaaaca cacacacact ggacagtaga tgggccgaca cacacttggc ccgagttcct   16380
```

-continued

```
ccatttccct ggcctgcccc ccaccccaa cctgtcccac ccccgtgccc cctccttacc   16440
ccgcaggacg ggcctacagg ggggtctccc ctcacccctg cacccccagc tgggggagct   16500
ggctctgccc cgacctcctt caccagggt tggggcccct tccctggag cccgtgggtg   16560 cacctgttac tgttgggctt ccactgaga tctactggat aaagaataaa gttctattta   16620
ttctacacat gcctccagcc ttgctgcctc cacccctcc tcttggcgtc tggtctgggg   16680
gcttgggatg ggtttcgtca tgtgctctgg gcctgtgatg gccaggaatg agcactgggg   16740
ccaaggggct ggccagggca cccttccaag ctgccttctg aggcttacct tgtgctgggg   16800
tctttggaga tgctgagaag gagaaagtcc tgccccttgg gaagccctca gtctggggat   16860
ccacactgcc catgtcaagg agccccagtc tgggagtggg agagaagagg aggaaagctg   16920
cccccacctt cagggaaccc ccagtctgag ggaggaagcc ggagccaccc ctagacattt   16980
ctggtccttg ggaagccttc                                              17000
```

<210> SEQ ID NO 4
<211> LENGTH: 459
<212> TYPE: PRT
<213> ORGANISM: Rattus norvegicus

<400> SEQUENCE: 4

```
Met Tyr Glu Ser Val Glu Val Gly Gly Leu Thr Pro Ala Pro Asn Pro
  1               5                  10                  15

Phe Leu Val Val Asp Phe Tyr Asn Gln Asn Arg Ala Cys Leu Leu Gln
                 20                  25                  30

Glu Lys Gly Leu Pro Ala Pro Gly Pro Tyr Ser Thr Pro Leu Arg Thr
             35                  40                  45

Pro Leu Trp Asn Gly Ser Asn His Ser Ile Glu Thr Gln Ser Ser Ser
         50                  55                  60

Ser Glu Glu Ile Val Pro Ser Pro Pro Ser Pro Pro Leu Pro Arg
 65                  70                  75                  80

Ile Tyr Lys Pro Cys Phe Val Cys Gln Asp Lys Ser Ser Gly Tyr His
                 85                  90                  95

Tyr Gly Val Ser Ala Cys Glu Gly Cys Lys Gly Phe Phe Arg Arg Ser
            100                 105                 110

Ile Gln Lys Asn Met Val Tyr Thr Cys His Arg Asp Lys Asn Cys Ile
        115                 120                 125

Ile Asn Lys Val Thr Arg Asn Arg Cys Gln Tyr Cys Arg Leu Gln Lys
    130                 135                 140

Cys Phe Glu Val Gly Met Ser Lys Glu Ser Val Arg Asn Asp Arg Asn
145                 150                 155                 160

Lys Lys Lys Lys Glu Thr Pro Lys Pro Glu Cys Ser Glu Ser Tyr Thr
                165                 170                 175

Leu Thr Pro Glu Val Gly Glu Leu Ile Glu Lys Val Arg Lys Ala Asn
            180                 185                 190

Gln Glu Thr Phe Pro Ala Leu Cys Gln Leu Gly Lys Tyr Thr Thr Asn
        195                 200                 205

Asn Ser Ser Glu Gln Arg Val Ser Leu Asp Ile Asp Leu Trp Asp Lys
    210                 215                 220

Phe Ser Glu Leu Ser Thr Lys Cys Ile Ile Lys Thr Val Glu Phe Ala
225                 230                 235                 240

Lys Gln Leu Pro Gly Phe Thr Thr Leu Thr Ile Ala Asp Gln Ile Thr
                245                 250                 255

Leu Leu Lys Ala Ala Cys Leu Asp Ile Leu Ile Leu Arg Ile Cys Thr
```

-continued

```
                  260                     265                     270

Arg Tyr Thr Pro Glu Gln Asp Thr Met Thr Phe Ser Asp Gly Leu Thr
                275                     280                     285

Leu Asn Arg Thr Gln Met His Asn Ala Gly Phe Gly Pro Leu Thr Asp
                290                     295                     300

Leu Val Phe Ala Phe Ala Asn Gln Leu Leu Pro Leu Glu Met Asp Asp
        305                     310                     315                     320

Ala Glu Thr Gly Leu Leu Ser Ala Ile Cys Leu Ile Cys Gly Asp Arg
                        325                     330                     335

Gln Asp Leu Glu Gln Pro Asp Lys Val Asp Met Leu Gln Glu Pro Leu
                        340                     345                     350

Leu Glu Ala Leu Lys Val Tyr Val Arg Lys Arg Arg Pro Ser Gln Pro
                        355                     360                     365

His Met Phe Pro Lys Met Leu Met Lys Ile Thr Asp Leu Arg Ser Ile
                370                     375                     380

Ser Ala Lys Gly Ala Glu Arg Val Ile Thr Leu Lys Met Glu Ile Pro
        385                     390                     395                     400

Gly Ser Met Pro Pro Leu Ile Gln Glu Met Leu Glu Asn Ser Glu Gly
                        405                     410                     415

Leu Asp Thr Leu Ser Gly Gln Ser Gly Gly Gly Thr Arg Asp Gly Gly
                        420                     425                     430

Gly Leu Ala Pro Pro Gly Ser Cys Ser Pro Ser Leu Ser Pro Ser
                435                     440                     445

Ser His Arg Ser Ser Pro Ala Thr Gln Ser Pro
                450                     455
```